United States Patent
Behfar et al.

(10) Patent No.: US 9,884,090 B2
(45) Date of Patent: Feb. 6, 2018

(54) USING NUCLEIC ACIDS ENCODING NAP-2 AND TGF-ALPHA POLYPEPTIDES TO IMPROVE CARDIAC FUNCTION

(71) Applicant: Mayo Foundation for Medical Education and Research, Rochester, MN (US)

(72) Inventors: Atta Behfar, Rochester, MN (US); Andre Terzic, Rochester, MN (US); Ruben Jose Crespo-Diaz, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 14/916,548

(22) PCT Filed: Sep. 3, 2014

(86) PCT No.: PCT/US2014/053860
§ 371 (c)(1),
(2) Date: Mar. 3, 2016

(87) PCT Pub. No.: WO2015/034897
PCT Pub. Date: Mar. 12, 2015

(65) Prior Publication Data
US 2016/0206697 A1    Jul. 21, 2016

Related U.S. Application Data

(60) Provisional application No. 61/873,122, filed on Sep. 3, 2013.

(51) Int. Cl.
| | | |
|---|---|---|
| A61K 48/00 | (2006.01) | |
| A61P 9/10 | (2006.01) | |
| A61K 38/19 | (2006.01) | |
| G01N 33/68 | (2006.01) | |
| A61K 38/18 | (2006.01) | |
| A61K 38/45 | (2006.01) | |
| C07K 14/52 | (2006.01) | |
| C07K 14/495 | (2006.01) | |

(52) U.S. Cl.
CPC ........ *A61K 38/195* (2013.01); *A61K 38/1841* (2013.01); *A61K 38/45* (2013.01); *G01N 33/6887* (2013.01); *A61K 48/005* (2013.01); *C07K 14/495* (2013.01); *C07K 14/522* (2013.01); *C12Y 207/10001* (2013.01); *G01N 2800/325* (2013.01); *G01N 2800/50* (2013.01)

(58) Field of Classification Search
None
See application file for complete search history.

(56) References Cited

U.S. PATENT DOCUMENTS

| | | |
|---|---|---|
| 2004/0009940 A1 | 1/2004 | Coleman |
| 2006/0265043 A1 | 11/2006 | Mandrusov |
| 2007/0038173 A1 | 2/2007 | Simpson |
| 2012/0308565 A1 | 12/2012 | Lillard |

FOREIGN PATENT DOCUMENTS

| | | |
|---|---|---|
| WO | WO2001040251 | 6/2001 |
| WO | WO 2004045530 | 6/2004 |
| WO | WO2005103720 | 11/2005 |
| WO | WO 2008112424 | 9/2008 |
| WO | WO 2011113905 | 9/2011 |
| WO | WO2012058313 | 6/2012 |
| WO | WO 2013036285 | 3/2013 |
| WO | WO2013113060 | 8/2013 |

OTHER PUBLICATIONS

Manukyan et al, 2011. Surgery. 150:339-346.*
Rosengart et al, 2012. Innovations. 7: 173-179.*
Arrell et al., "Cardioinductive network guiding stem cell differentiation revealed by proteomic cartography of tumor necrosis factor alpha-primed endodermal secretome," *Stem Cells*, 26(2):387-400, Epub Nov. 8, 2007.
Crespo-Diaz et al., "Platelet lysate consisting of a natural repair proteome supports human mesenchymal stem cell proliferation and chromosomal stability," *Cell Transplant.*, 20(6):797-811, Epub Nov. 19, 2010.
Ehlert et al., "Novel C-terminally truncated isoforms of the CXC chemokine beta-thromboglobulin and their impact on neutrophil functions," *J Immunol.*, 161(9):4975-4982, Nov. 1, 1998.
GenBank® Accession No. D12763.1, "*Homo sapiens* mRNA for ST2 protein," Jan. 23, 2003, 2 pages.
GenBank® Accession No. NP_001054.1, "serotransferrin precursor [*Homo sapiens*]," Sep. 10, 2012, 3 pages.
GenBank® Accession No. NP_001502.1, "growth-regulated alpha protein precursor [*Homo sapiens*]," Sep. 15, 2012, 3 pages.
GenBank® Accession No. NP_002413.1, "stromelysin-1 preproprotein [*Homo sapiens*]," Sep. 30, 2012, 3 pages.
GenBank® Accession No. NP_002505.1, "protein NOV homolog precursor [*Homo sapiens*]," Sep. 30, 2012, 3 pages.
GenBank® Accession No. NP_003227.1, "protransforming growth factor alpha isoform 1 preproprotein [*Homo sapiens*]," Oct. 28, 2012, 3 pages.
GenBank® Accession No. NP_005615.2, "C-C motif chemokine 25 isoform 1 precursor [*Homo sapiens*]," Nov. 25, 2012, 3 pages.
GenBank® Accession No. NP_068575.1, "interleukin-21 isoform 1 precursor [*Homo sapiens*]," Sep. 15, 2012, 3 pages.

(Continued)

*Primary Examiner* — Zachary Howard
(74) *Attorney, Agent, or Firm* — Mueting, Raasch & Gebhardt, P.A.

(57) ABSTRACT

This document provides methods and materials for reducing the risk of major adverse cardiac events. For example, methods and materials for identifying patients at risk of experiencing a major adverse cardiac event as well as methods and material for treating patients at risk of experiencing a major adverse cardiac event (e.g., patients who underwent percutaneous coronary intervention (PCI) for ST-elevation myocardial infarction (STEMI)) are provided.

6 Claims, 15 Drawing Sheets

(56) References Cited

OTHER PUBLICATIONS

GenBank® Accession No. BAA02233, "ST2 protein [*Homo sapiens*]," Jan. 23, 2003, 2 pages.
GenBank® Accession No. NM_000301, "*Homo sapiens* plasminogen (PLG), transcript variant 1, mRNA," Sep. 22, 2012, 6 pages.
GenBank® Accession No. NM_001005915.1, "*Homo sapiens* v-erb-b2 erythroblastic leukemia viral oncogene homolog 3 (avian) (ERBB3), transcript variant s, mRNA," Sep. 16, 2012, 4 pages.
GenBank® Accession No. NM_001039667.1, "*Homo sapiens* angiopoietin-like 4 (ANGPTL4), transcript variant 3, mRNA," Oct. 28, 2012, 5 pages.
GenBank® Accession No. NM_001063.3, "*Homo sapiens* transferrin (TF), mRNA," Sep. 10, 2012, 6 pages.
GenBank® Accession No. NM_001065, "*Homo sapiens* tumor necrosis factor receptor superfamily, member 1A (TNFRSF1A), mRNA," Sep. 10, 2012, 6 pages.
GenBank® Accession No. NM_001066, "*Homo sapiens* tumor necrosis factor receptor superfamily, member 1B (TNFRSF1B), mRNA," Sep. 9, 2012, 6 pages.
GenBank® Accession No. NM_001511, "*Homo sapiens* chemokine (C-X-C motif) ligand 1 (melanoma growth stimulating activity, alpha) (CXCL1), transcript variant 1, mRNA," Sep. 15, 2012, 5 pages.
GenBank® Accession No. NM_001982.3, "*Homo sapiens* v-erb-b2 erythroblastic leukemia viral oncogene homolog 3 (avian) (ERBB3), transcript variant 1, mRNA," Sep. 16, 2012, 9 pages.
GenBank® Accession No. NM_002422, "*Homo sapiens* matrix metallopeptidase 3 (stromelysin 1, progelatinase) (MMP3), mRNA," Sep. 30, 2012, 5 pages.
GenBank® Accession No. NM_002514, "*Homo sapiens* nephroblastoma overexpressed (NOV), mRNA," Sep. 30, 2012, 5 pages.
GenBank® Accession No. NM_002704, "*Homo sapiens* pro-platelet basic protein (chemokine (C-X-C motif) ligand 7) (PPBP), mRNA," Oct. 21, 2012, 5 pages.
GenBank® Accession No. NM_003236, "*Homo sapiens* transforming growth factor, alpha (TGFA), transcript variant 1, mRNA," Oct. 28, 2012, 5 pages.
GenBank® Accession No. NM_003255.4, "*Homo sapiens* TIMP metallopeptidase inhibitor 2 (TIMP2), mRNA," Sep. 16, 2012, 6 pages.
GenBank® Accession No. NM_004079.4, "*Homo sapiens* cathepsin S (CTSS), transcript variant 1, mRNA," Oct. 14, 2012, 5 pages.
GenBank® Accession No. NM_005624, "*Homo sapiens* chemokine (C-C motif) ligand 25 (CCL25), transcript variant 1, mRNA," Nov. 25, 2012, 4 pages.
GenBank® Accession No. NM_006072, "*Homo sapiens* chemokine (C-C motif) ligand 26 (CCL26), mRNA," Nov. 10, 2012, 4 pages.
GenBank® Accession No. NM_012242, "*Homo sapiens* dickkopf 1 homolog (Xenopus laevis) (DKK1), mRNA," Sep. 10, 2012, 4 pages.
GenBank® Accession No. NM_013409.2, "*Homo sapiens* follistatin (FST), transcript variant FST344, mRNA," Sep. 16, 2012, 4 pages.
GenBank® Accession No. NM_021803, "*Homo sapiens* interleukin 21 (IL21), transcript variant 1, mRNA," Sep. 15, 2012, 4 pages.
GenBank® Accession No. NM_139314.1, "*Homo sapiens* angiopoietin-like 4 (ANGPTL4), transcript variant 1, mRNA," Oct. 28, 2012, 5 pages.
GenBank® Accession No. NP_000292, "plasminogen isoform 1 precursor [*Homo sapiens*]," Sep. 22, 2012, 3 pages.
GenBank® Accession No. NP_001005915.1, "receptor tyrosine-protein kinase erbB-3 isoform s precursor [*Homo sapiens*]," Aug. 12, 2012, 3 pages.

GenBank® Accession No. NP_001034756.1, "angiopoietin-related protein 4 isoform b precursor [*Homo sapiens*]," Jul. 29, 2012, 3 pages.
GenBank® Accession No. NP_001056.1, "tumor necrosis factor receptor superfamily member 1A precursor [*Homo sapiens*]," Aug. 30, 2012, 4 pages.
GenBank® Accession No. NP_001057.1, "tumor necrosis factor receptor superfamily member 1B precursor [*Homo sapiens*]," Aug. 26, 2012, 3 pages.
GenBank® Accession No. NP_001973.2, "receptor tyrosine-protein kinase erbB-3 isoform 1 precursor [*Homo sapiens*]," Aug. 12, 2012, 4 pages.
GenBank® Accession No. NP_002695.1, "platelet basic protein preproprotein [*Homo sapiens*]," Jul. 29, 2012, 3 pages.
GenBank® Accession No. NP_003246.1, "metalloproteinase inhibitor 2 precursor [*Homo sapiens*]," Sep. 2, 2013, 3 pages.
GenBank® Accession No. NP_004070.3, "cathepsin S isoform 1 preproprotein [*Homo sapiens*]," Jun. 26, 2012, 3 pages.
GenBank® Accession No. NP_006063.1, "C-C motif chemokine 26 precursor [*Homo sapiens*]," Jun. 2, 2013, 3 pages.
GenBank® Accession No. NP_036374.1, "dickkopf-related protein 1 precursor [*Homo sapiens*]," Aug. 19, 2012, 3 pages.
GenBank® Accession No. NP_037541.1, "follistatin isoform FST344 precursor [*Homo sapiens*]," Aug. 5, 2012.
GenBank® Accession No. NP_647475.1, "angiopoietin-related protein 4 isoform a precursor [*Homo sapiens*]," Jul. 29, 2012, 3 pages.
Kushner et al., "2009 focused updates: ACC/AHA guidelines for the management of patients with ST-elevation myocardial infarction (updating the 2004 guideline and 2007 focused update) and ACC/AHA/SCAI guidelines on percutaneous coronary intervention (updating the 2005 guideline and 2007 focused update) a report of the American College of Cardiology Foundation/American Heart Association Task Force on Practice Guidelines," *J Am Coll Cardiol.*, 54(23):2205-2241, Dec. 1, 2009.
Morrow et al., "Application of the TIMI risk score for ST-elevation MI in the National Registry of Myocardial Infarction 3," *JAMA.*, 286(11):1356-1359, Sep. 19, 2001.
Morrow et al., "TIMI risk score for ST-elevation myocardial infarction: A convenient, bedside, clinical score for risk assessment at presentation: An intravenous nPA for treatment of infarcting myocardium early II trial substudy," *Circulation*, 102(17):2031-2037, Oct. 24, 2000.
Singh et al., "Correlates of procedural complications and a simple integer risk score for percutaneous coronary intervention," *J Am Coll Cardiol.*, 40(3):387-393, Aug. 7, 2002.
Smoot et al., "Cytoscape 2.8: new features for data integration and network visualization," *Bioinformatics*, 27(3):431-432, Epub Dec. 12, 2010.
Zlatkovic-Lindor et al., "ATP-sensitive K(+) channel-deficient dilated cardiomyopathy proteome remodeled by embryonic stem cell therapy," *Stem Cells*, 28(8):1355-1367, Aug. 2010.
International Search Report and Written Opinion for PCT/US2014/053860, dated Feb. 3, 2015, 13 pages.
International Preliminary Report on Patentability for PCT/US2014/053860, dated Mar. 8, 2016, 9 pages.
Invitation to Pay for PCT/US2014/053860, dated Dec. 5, 2014, 3 pages.
Andreoli and Parissis, "Chapter 6 : Biomarkers in Congestive Heart Failure," Biomarkers in Cardiovascular Diseases., 101-445, 2014.
European Search Report for European Application No. 14842064.9, dated Feb. 14, 2017, 10 pages.
Smith et al., "Increased Levels of Neutrophil-Activating Peptide-2 in Acute Coronary Syndromes Possible Role of Platelet-Mediated Vascular Inflammation," J American College Cargiology., 48(8):1591-1599, Oct. 17, 2006.
Extended European Search Report for European Application No. 14842064.9, dated Jun. 8, 2017, 19 pages.
Guler et al. "Myocardial fibrosis detected by cardiac magnetic resonance imaging in heart failure: Impact on remodeling, diastolic function and BNP levels," Anadolu Kardiyol Derg., 11(1):71-76, Feb. 1, 2011.

(56) References Cited

OTHER PUBLICATIONS

Herrmann et al. "Transforming Growth Factor—Enhances Stem Cell-Mediated Postischemic Myocardial Protection," Ann Thorac Surg., 92(5):1719-1725, Nov. 2011.

* cited by examiner

Figure 6
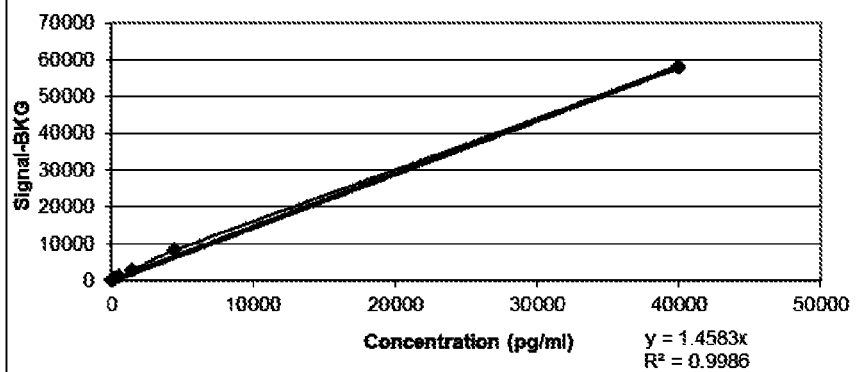
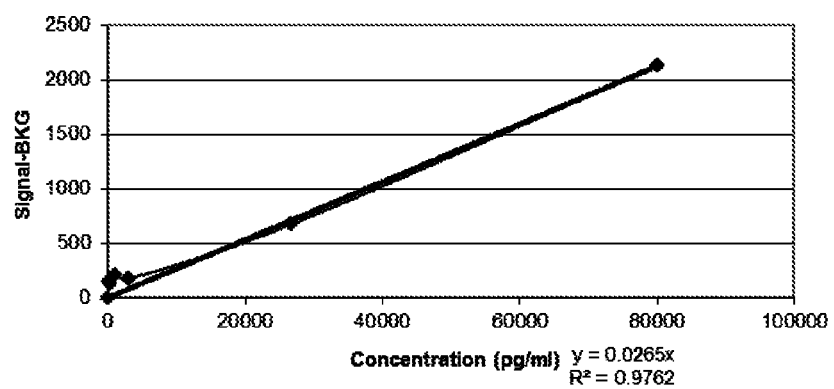
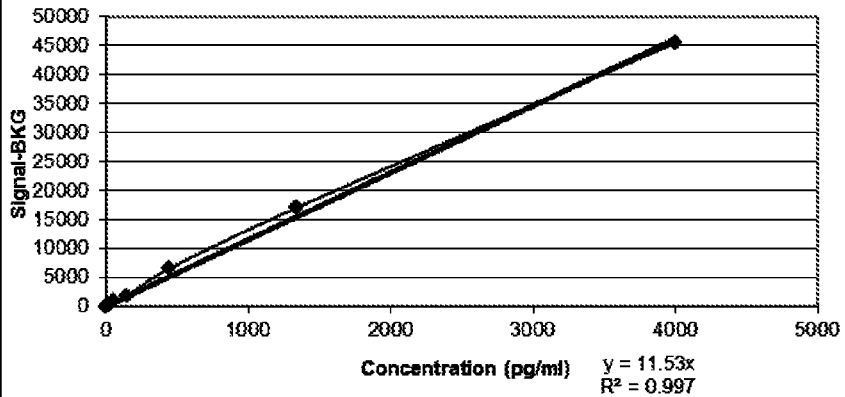

Figure 8
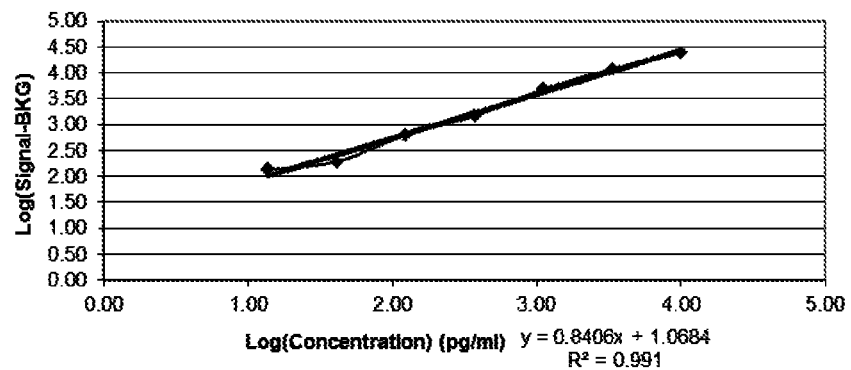
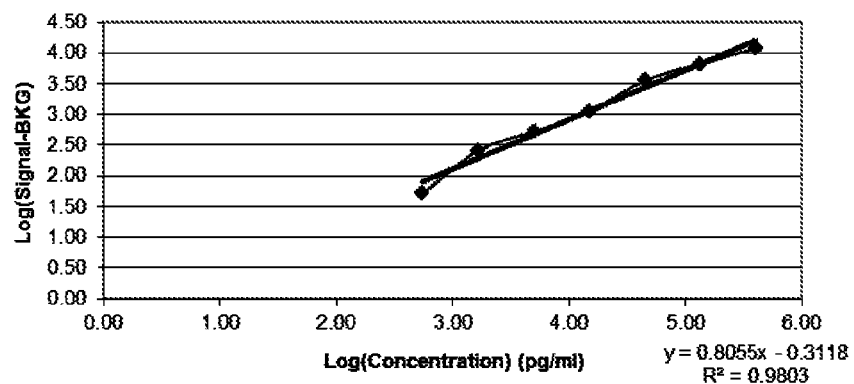
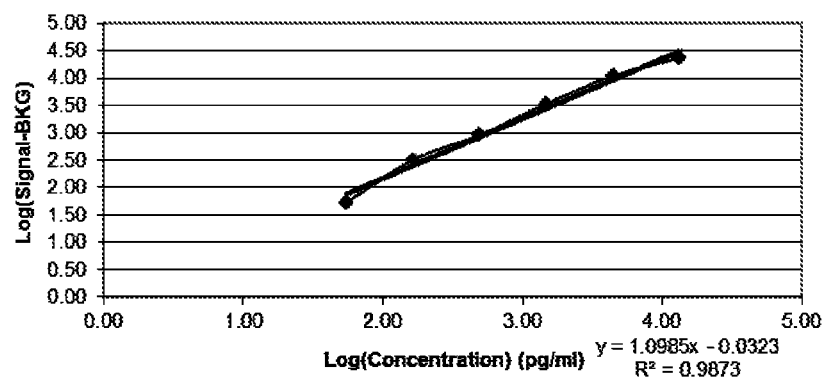

Figure 13

| Biomarker | Sensitivity | Specificity | Biological role in MI |
|---|---|---|---|
| Eotaxin-3 | 70 | 70 | Chemoattraction of eosinophils. Unknown role in MI. |
| Cathepsin S | 71 | 73 | Increased elastolytic and collagenolytic activity in diseased arteries. Induced expression during atherogenesis. |
| DKK-1 | 64 | 82 | Increased serum levels in patients suffering angina. Expressed in atherosclerotic plaques, may contribute to inflammatory process. |
| Follistatin | 86 | 55 | No biological role has been described to Follistatin in MI; however Follistatin family member Fstl1 is cardioprotective in ischemia reperfusion. |
| ST-2 | 93 | 45 | Increased levels in patients with MI. Blocks antihypertrophic signaling in pressure overload. |
| GROa | 64 | 82 | Upregulated in the heart following MI. |
| IL-21 | 92 | 55 | Augments T cell response during inflammation. Limited data for role in MI. |
| NOV | 100 | 56 | Expression detected in cardiomyocytes and smooth muscle cells. Limited data for MI role. |
| Transferrin | 86 | 76 | Lipid perioxidation and pro-oxidtative environment in atherosclerotic lesions by iron. |
| TIMP-2 | 79 | 64 | Attenuates atherosclerotic plaque development and reduces MMP activity. |
| TNFRI | 80 | 64 | Provide cytoprotection in ischemia/reperfusion injury. May contribute to necrosis and apoptosis during MI. |
| TNFRII | 71 | 73 | See above |
| ErB3 | 50 | 100 | Absent in myocardium postnatally. No role in MI to date. |

USING NUCLEIC ACIDS ENCODING NAP-2 AND TGF-ALPHA POLYPEPTIDES TO IMPROVE CARDIAC FUNCTION

CROSS-REFERENCE TO RELATED APPLICATIONS

This application is a U.S. national stage under 35 U.S.C. §371 of International Application No. PCT/US2014/053860, filed on Sep. 3, 2014, which claims the benefit of U.S. Provisional Application Ser. No. 61/873,122, filed on Sep. 3, 2013. The disclosure of the prior applications is considered part of (and is incorporated by reference in) the disclosure of this application.

BACKGROUND

1. Technical Field

This document relates to methods and materials for reducing the risk of major adverse cardiac events. For example, this document provides methods and materials for identifying patients at risk of experiencing a major adverse cardiac event as well as methods and material for treating patients at risk of experiencing a major adverse cardiac event (e.g., patients who underwent percutaneous coronary intervention (PCI) for ST-elevation myocardial infarction (STEMI)).

2. Background Information

Strategies to rapidly re-perfuse patients presenting with STEMI have considerably improved acute survivorship. These patients, however, harbor a significant long-term risk of experiencing a major cardiac adverse event following, for example, PCI for STEMI.

SUMMARY

This document provides methods and materials for reducing the risk of major adverse cardiac events. For example, this document provides methods and materials for identifying patients at risk of experiencing a major adverse cardiac event as well as methods and material for treating patients at risk of experiencing a major adverse cardiac event (e.g., patients who underwent PCI for STEMI).

As described herein, a STEMI patient who underwent PCI can be assessed to determine whether or not that patient has an increased risk of experiencing a major adverse cardiac event as opposed to being identified as being unlikely to experience a major adverse cardiac event. For example, the expression profiles of one or more (e.g., one, two, three, four, five, six, seven, eight, nine, ten, eleven, 12, 13, 14, 15, 16, 17, 18, or 19) of the following polypeptides can be used to identify patients at risk of experiencing a major adverse cardiac event: eotaxin-3, cathepsin-S, Dickopf-1 (DKK-1), follistatin, suppression of tumorigenicity-2 (ST-2), GRO-alpha (GRO-α), interleukin-21 (IL-21), nephroblastoma overexpressed (NOV), transferrin, tissue inhibitor of metallopeptidase-2 (TIMP-2), tumor necrosis factor receptor-1 and -2 (TNFαRI and II), erythroblastic leukemia viral oncogene-3 (ErBb3), neutrophil-activating protein-2 (NAP-2), angiostatin, chemokine ligand-25 (CCL25), angiopoietin like-4 (ANGPTL4), matrix metalloproteinase-3 (MMP-3), and transforming growth factor-α (TGF-α). In some cases, a myocardial infarction patient or a STEMI patient who underwent PCI can be treated by administering a NAP-2 polypeptide or a nucleic acid encoding a NAP-2 polypeptide to the patient. In some cases, a patient to be treated can be identified for treatment by assessing expression profiles as described herein. In some cases, the methods and materials provided herein can be used to monitor or confirm that a particular myocardial infarction treatment option (e.g., treatment with a NAP-2 polypeptide or a nucleic acid encoding a NAP-2 polypeptide) is effective.

In general, one aspect of this document features a method for improving cardiac function. The method comprises, or consists essentially of, administering a composition comprising a NAP-2 polypeptide or a nucleic acid encoding a NAP-2 polypeptide to a mammal, thereby improving cardiac function of said mammal. The composition can comprise the NAP-2 polypeptide. The composition can comprise the nucleic acid encoding a NAP-2 polypeptide. The mammal can be a human. The mammal can be a human patient who underwent percutaneous coronary intervention for ST-elevation myocardial infarction. The method can comprise administering the composition during a percutaneous coronary intervention. The method can comprise administering a TGF-α polypeptide or a nucleic acid encoding a TGF-α polypeptide to the mammal.

In another aspect, this document features a method for improving cardiac function. The method comprises, or consists essentially of, administering a composition comprising a TGF-α polypeptide or a nucleic acid encoding a TGF-α polypeptide to a mammal, thereby improving cardiac function of said mammal. The composition can comprise the TGF-α polypeptide. The composition can comprise the nucleic acid encoding a TGF-α polypeptide. The mammal can be a human. The mammal can be a human patient who underwent percutaneous coronary intervention for ST-elevation myocardial infarction. The method can comprise administering the composition during a percutaneous coronary intervention.

In another aspect, this document features a method for improving cardiac function. The method comprises, or consists essentially of, administering a composition comprising a ErBb3 polypeptide or a nucleic acid encoding a ErBb3 polypeptide to a mammal, thereby improving cardiac function of said mammal. The composition can comprise the ErBb3 polypeptide. The composition can comprise the nucleic acid encoding a ErBb3 polypeptide. The mammal can be a human. The mammal can be a human patient who underwent percutaneous coronary intervention for ST-elevation myocardial infarction. The method can comprise administering the composition during a percutaneous coronary intervention.

In another aspect, this document features a method for improving cardiac function. The method comprises, or consists essentially of, administering a composition comprising an inhibitor of eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, and/or MMP-3 polypeptide expression or activity to a mammal, thereby improving cardiac function of said mammal. The mammal can be a human. The mammal can be a human patient who underwent percutaneous coronary intervention for ST-elevation myocardial infarction. The method can comprise administering the composition during a percutaneous coronary intervention.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1A (LAD; left panel) is an angiographic depiction of an occlusive thrombus in the left anterior descending artery. Middle and right panels depict the steps taken to aspirate clot and coronary blood out of the occluded vessel. FIG. 1B is a depiction of a clot extraction via a coronary aspiration catheter and collection of sample in a vacuum syringe. High throughput proteomic assessment documents the protein content of the occluded coronary blood at the time of reperfusion in STEMI.

FIG. 2A provides the Mayo Clinic Risk Model of major adverse cardiac events score for each patient at the time of STEMI. FIG. 2B provides the percentage of patients receiving respective pharmacologic agent. FIG. 2C provides echocardiographic parameters. FIG. 2D provides ejection fraction change and survival at two years following STEMI.

FIG. 6 contains bar graphs plotting standard curves for the indicated cytokine.

FIG. 8 contains bar graphs plotting standard curves for the indicated cytokine.

FIG. 13 contains a table with cytokine sensitivity and specificity along with pathobiological role in myocardial infarction.

FIG. 15A contains a time-line of animal experiments: data collection, surgery, and therapy. FIG. 15B contains data of PTAH fibrosis staining and quantification in saline (n=20) and growth factor treated groups (n=10). FIG. 15C contains data of an echocardiographic analysis of both groups demonstrating functional benefit in growth factor treated mice (n=6) compared to saline (n=12).

DETAILED DESCRIPTION

Figure 1:
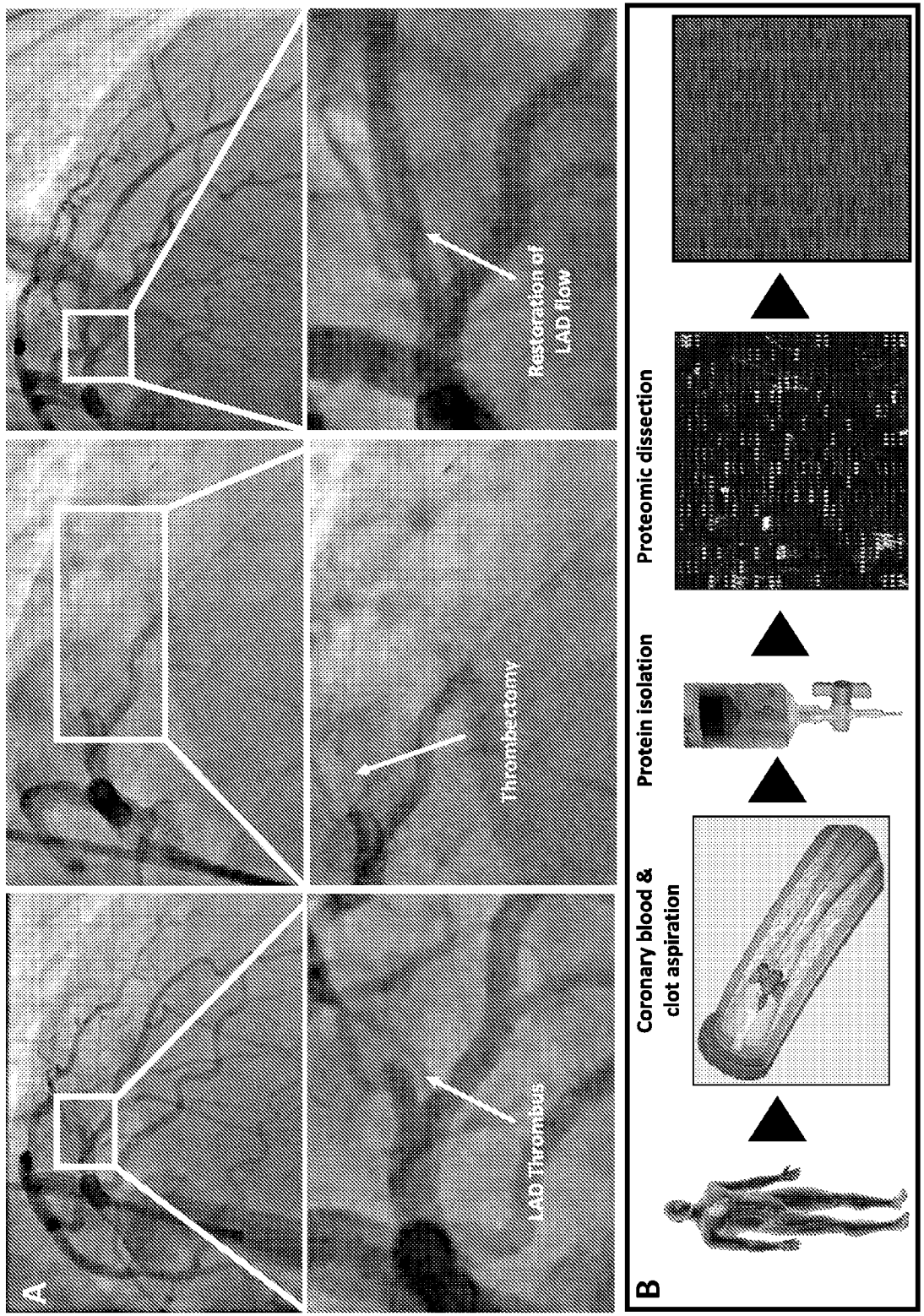
FIGS. 1A and 1B demonstrate that coronary thrombus aspiration during STEMI provides the serological resource for high throughput proteomic assessment.

This document provides methods and materials for reducing the risk of major adverse cardiac events. For example, this document provides methods and materials for identifying patients at risk of experiencing a major adverse cardiac event as well as methods and material for treating patients at risk of experiencing a major adverse cardiac event (e.g., patients who underwent PCI for STEMI). Examples of major adverse cardiac events include, without limitation, death, heart failure, recurrent myocardial infarction, and repeat hospitalization for cardiac-related events.

As described herein, the expression levels of one or more (e.g., one, two, three, four, five, six, seven, eight, nine, ten, eleven, 12, 13, 14, 15, 16, 17, 18, or 19) of the following polypeptides within a serum sample obtained from a myocardial infarction patient (e.g., a STEMI patient who underwent PCI) can be used to identify patients at risk of experiencing a major adverse cardiac event: eotaxin-3, cathepsin-S, DKK-1, follistatin, ST-2, GRO-α, IL-21, NOV, transferrin, TIMP-2, TNFαRI, TNFαRII, ErBb3, NAP-2, angiostatin, CCL25, ANGPTL4, MMP-3, and TGF-α. For example, if a myocardial infarction patient (e.g., a STEMI patient who underwent PCI) contains serum (e.g., coronary serum) with an elevated level of one or more of eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, and MMP-3, then the patient can be classified as being at risk of experiencing a major adverse cardiac event. In some cases, if a myocardial infarction patient (e.g., a STEMI patient who underwent PCI) contains serum (e.g., coronary serum) with a reduced level of one or more of ErBb3, NAP-2, and TGF-α, then the patient can be classified as being at risk of experiencing a major adverse cardiac event. In some cases, if a myocardial infarction patient (e.g., a STEMI patient who underwent PCI) contains serum (e.g., coronary serum) with an elevated level of one or more of eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, and MMP-3 and a reduced level of one or more of ErBb3, NAP-2, and TGF-α, then the patient can be classified as being at risk of experiencing a major adverse cardiac event.

A human eotaxin-3 polypeptide can have the amino acid sequence set forth in GenBank® Accession No. NP_006063.1 (GI No. 10344) and can be encoded by the nucleic acid sequence set forth in GenBank® Accession No. NM_006072 (GI No. 10344). A human cathepsin-S polypeptide can have the amino acid sequence set forth in GenBank® Accession No. NP_004070.3 (GI No. 1520) and can be encoded by the nucleic acid sequence set forth in GenBank® Accession No. NM_004079.4 (GI No. 1520). A human DKK-1 polypeptide can have the amino acid sequence set forth in GenBank® Accession No. NP_036374.1 (GI No. 22943) and can be encoded by the nucleic acid sequence set forth in GenBank® Accession No. NM_012242 (GI No. 22943). A human follistatin polypeptide can have the amino acid sequence set forth in GenBank® Accession No. NP_037541.1 (GI No. 10468) and can be encoded by the nucleic acid sequence set forth in GenBank® Accession No. NM_013409.2 (GI No. 10468). A human ST-2 polypeptide can have the amino acid sequence set forth in GenBank® Accession No. BAA02233 (GI No. 6761) and can be encoded by the nucleic acid sequence set forth in GenBank® Accession No D12763.1 (GI No 6761). A human GRO-α polypeptide can have the amino acid sequence set forth in GenBank® Accession No. NP_001502.1 (GI No. 2919) and can be encoded by the nucleic acid sequence set forth in GenBank® Accession No. NM_001511 (GI No. 2919). A human IL-21 polypeptide can have the amino acid sequence set forth in GenBank® Accession No. NP_068575.1 (GI No. 59067) and can be encoded by the nucleic acid sequence set forth in GenBank® Accession No. NM_021803 (GI No. 59067). A human NOV polypeptide can have the amino acid sequence set forth in GenBank® Accession No. NP_002505.1 (GI No. 4856) and can be encoded by the nucleic acid sequence set forth in GenBank® Accession No. NM_002514 (GI No. 4856). A human transferrin polypeptide can have the amino acid sequence set forth in GenBank® Accession No. NP_001054.1 (GI No. 7018) and can be encoded by the nucleic acid sequence set forth in GenBank® Accession No. NM_001063.3 (GI No. 7018). A human TIMP-2 polypeptide can have the amino acid sequence set forth in GenBank® Accession No. NP_003246.1 (GI No. 7077) and can be encoded by the nucleic acid sequence set forth in GenBank® Accession No. NM_003255.4 (GI No. 7077). A human TNFαRI polypeptide can have the amino acid sequence set forth in GenBank® Accession No. NP_001056.1 (GI No. 7132) and can be encoded by the nucleic acid sequence set forth in GenBank® Accession No. NM_001065 (GI No. 7132). A human TNFαRII polypeptide can have the amino acid sequence set forth in GenBank® Accession No. NP_001057.1 (GI No. 7133) and can be encoded by the nucleic acid sequence set forth in GenBank® Accession No. NM_001066 (GI No. 7133). A human ErBb3 polypeptide can have the amino acid sequence set forth in GenBank® Accession No. NP_001005915.1 or NP_001973.2 (GI No. 2065) and can be encoded by the nucleic acid sequence set forth in GenBank® Accession No. NM_001005915.1 or NM_001982.3 (GI No. 2065). A human NAP-2 polypeptide can have the amino acid sequence set forth in GenBank® Accession No. NP_002695.1 (GI No. 5473) and can be encoded by the nucleic acid sequence set forth in GenBank® Accession No. NM_002704 (GI No. 5473). A human angiostatin polypeptide can have the amino acid sequence set forth in GenBank® Accession No. NP_000292 (GI No. 5340) and can be encoded by the nucleic acid sequence set forth in GenBank® Accession No. NM_000301 (GI No. 5340). A human CCL25 polypeptide can have the amino acid sequence set forth in GenBank® Accession No. NP_005615.2 (GI No. 6370) and can be encoded by the nucleic acid sequence set forth in GenBank® Accession No. NM_005624 (GI No. 6370). A human ANGPTL4 polypeptide can have the amino acid sequence set forth in GenBank® Accession No. NP_001034756.1 or NP_647475.1 (GI No. 51129) and can be encoded by the nucleic acid sequence set forth in GenBank® Accession No. NM_001039667.1 or NM_139314.1 (GI No. 51129). A human MMP-3 polypeptide can have the amino acid sequence set forth in GenBank® Accession No. NP_002413.1 (GI No. 4314) and can be encoded by the nucleic acid sequence set forth in GenBank® Accession No. NM_002422 (GI No. 4314). A human TGF-α polypeptide can have the amino acid sequence set forth in GenBank® Accession No. NP_003227.1 (GI No. 7039) and can be encoded by the nucleic acid sequence set forth in GenBank® Accession No. NM_003236 (GI No. 7039).

The term "elevated level" as used herein with respect to the level of a polypeptide (e.g., an eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, or MMP-3 polypeptide) is any level that is greater than (e.g., at least about 10, 15, 20, or 25 percent greater than) a reference level for that polypeptide. The term "reduced level" as used herein with respect to the level of a polypeptide (e.g., an ErBb3, NAP-2, or TGF-α polypeptide) is any level that is less than (e.g., at least about 10, 15, 20, or 25 percent less than) a reference level for that polypeptide. The term "reference level" as used herein with respect to an eotaxin-3, cathepsin-S, DKK-1, follistatin, ST-2, GRO-α, IL-21, NOV, transferrin, TIMP-2, TNFαRI, TNFαRII, ErBb3, NAP-2, angiostatin, CCL25, ANGPTL4, MMP-3, or TGF-α polypeptide is the level of expression of that polypeptide typically observed by healthy humans or human patients with a low risk of experiencing a major adverse cardiac event. For example, a reference level of eotaxin-3 expression can be the average level of eotaxin-3 expression that is present in samples obtained from a random sampling of 50 healthy humans without evidence of cardiac problems. It will be appreciated that levels from comparable samples are used when determining whether or not a particular level is an elevated level or a reduced level. In some cases, the reference level of polypeptide expression can be a ratio of an expression value of that polypeptide in a sample to an expression value of a control polypeptide in the sample. A control polypeptide can be any polypeptide that has a minimal variation in expression level across various samples of the type for which the polypeptide serves as a control. For example, albumin polypeptides, C-reactive protein, or NT-proBNP polypeptides can be used as control polypeptides. In some cases, the reference level of polypeptide expression can be a ratio of an expression value of that polypeptide in a sample to the level of total protein in the sample.

An elevated level of eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, or MMP-3 polypeptide expression can be any level provided that the level is at least about 10 percent greater than (e.g., at least about 10, 15, 20, 25, 30, 35, 40, 45, 50, 55, 60 percent greater than) a corresponding reference level. For example, an elevated level of eotaxin-3 expression can be 15 or more percent greater than the reference level for eotaxin-3 expression.

A reduced level of ErBb3, NAP-2, or TGF-α polypeptide expression can be any level provided that the level is at least about 10 percent less than (e.g., at least about 10, 15, 20, 25, 30, 35, 40, 45, 50, 55, 60 percent less than) a corresponding reference level. For example, a reduced level of ErBb3 expression can be 15 or more percent less than the reference level for ErBb3 expression.

Any appropriate method can be used to determine expression levels of a polypeptide within a serum sample. For example, ELISA and other immunological-based assays can be used to determine the level of eotaxin-3, cathepsin-S, DKK-1, follistatin, ST-2, GRO-α, IL-21, NOV, transferrin, TIMP-2, TNFαRI, TNFαRII, ErBb3, NAP-2, angiostatin, CCL25, ANGPTL4, MMP-3, and/or TGF-α within a serum sample.

Once the levels of one or more of eotaxin-3, cathepsin-S, DKK-1, follistatin, ST-2, GRO-α, IL-21, NOV, transferrin, TIMP-2, TNFαRI, TNFαRII, ErBb3, NAP-2, angiostatin, CCL25, ANGPTL4, MMP-3, and/or TGF-α polypeptide expression in a sample from a patient is determined, then the levels can be compared to reference levels and used to evaluate the likelihood that the patient will experience a major adverse cardiac event. Those patients determined to be likely to experience a major adverse cardiac event as described herein can be subjected to increased monitoring and/or can be treated with an appropriate treatment option. For example, a patient identified as being likely to experience a major adverse cardiac event as described herein can be treated with aggressive pharmacotherapy (e.g., beta-adrenoceptor blockade treatments, treatment with angiotensin converting enzyme inhibitors, aldosterone antagonism treatments, and/or treatment with antiplatelet agents), hemodynamic support (e.g., intra-aortic balloon pump and/or mechanical augmentation of cardiac output), surgical intervention (e.g., coronary bypass grafting or left ventricular assist device placement), and/or device-based intervention (e.g., resychronization therapy or implantable cardiac defibrillators).

In some cases, a patient at risk of experiencing a major adverse cardiac event (e.g., a patient identified as being likely to experience a major adverse cardiac event as described herein) can be treated by increasing the level of NAP-2 polypeptide expression, by increasing the level of TGF-α polypeptide expression, or by increasing the levels of ErBb3 polypeptide expression, or by increasing the levels of a combination of any two of NAP-2 polypeptide expression, TGF-α polypeptide expression, and ErBb3 polypeptide expression (e.g. a combination of both NAP-2 polypeptide and TGF-α polypeptide expression). In some cases, a patient at risk of experiencing a major adverse cardiac event (e.g., a patient identified as being likely to experience a major adverse cardiac event as described herein) can be treated by increasing the level of NAP-2 polypeptide expression, by increasing the level of TGF-α polypeptide expression, and by increasing the level of ErBb3 polypeptide expression. An increased level of NAP-2 polypeptide, TGF-α polypeptide expression, and/or ErBb3 polypeptide expression can be used to reduce scar size and tissue remodeling and to improve cardiac function. For example, an area of fibrosis reflecting scar size from injury can be reduced by 10 to 100 percent (e.g., by 10 to 90 percent, by 10 to 80 percent, by 10 to 70 percent, by 10 to 60 percent, by 10 to 50 percent, by 20 to 100 percent, by 30 to 100 percent, or by 20 to 60 percent) following administration of NAP-2 polypeptides or nucleic acid encoding a NAP-2 polypeptide, TGF-α polypeptides or nucleic acid encoding a TGF-α polypeptide, ErBb3 polypeptides or nucleic acid encoding a ErBb3 polypeptide, or combinations thereof. In some cases, cardiac tissue remodeling can be reduced by 10 to 100 percent (e.g., by 10 to 90 percent, by 10 to 80 percent, by 10 to 70 percent, by 10 to 60 percent, by 10 to 50 percent, by 20 to 100 percent, by 30 to 100 percent, or by 20 to 60 percent) following administration of NAP-2 polypeptides or nucleic acid encoding a NAP-2 polypeptide, TGF-α polypeptides or nucleic acid encoding a TGF-α polypeptide, ErBb3 polypeptides or nucleic acid encoding a ErBb3 polypeptide, or combinations thereof. Examples of improved cardiac function include, without limitation, increased survivorship, reduced hospitalization, symptom-free tolerance of physical activity, improved global physical fitness, improved cardiac ejection fraction, improved cardiac output, improved stroke volume, improved cardiac mass index, and reduced scar size.

In some cases, the level of NAP-2 polypeptide, TGF-α polypeptide, and/or ErBb3 polypeptide expression can be increased by administering a composition containing NAP-2, TGF-α, and/or ErBb3 polypeptides. In some cases, the level of NAP-2 polypeptide, TGF-α polypeptide, and/or ErBb3 polypeptide expression can be increased by administering one or more nucleic acids (e.g., DNA or RNA) encoding a NAP-2 polypeptide, TGF-α polypeptide, and/or ErBb3 polypeptide to cells of the patient (e.g., resident or exogenously grown stem cells). Such a nucleic acid can encode a full-length NAP-2 polypeptide, a full-length TGF-α polypeptide, and/or a full-length ErBb3 polypeptide. In some cases, a nucleic acid encoding a fragment of a NAP-2 polypeptide, a TGF-α polypeptide, and/or an ErBb3 polypeptide that retains at least some biological activity can be used as described herein to reduce scar size and tissue remodeling and/or to improve cardiac function.

A nucleic acid encoding a NAP-2 polypeptide, a TGF-α polypeptide, and/or an ErBb3 polypeptide (or a fragment thereof) can be administered to a patient using any appropriate method. For example, a nucleic acid can be administered to a human using a vector such as a viral vector.

Vectors for administering nucleic acids (e.g., a nucleic acid encoding a NAP-2 polypeptide, a TGF-α polypeptide, and/or an ErBb3 polypeptide (or fragments thereof)) to a mammal are known in the art and can be prepared using standard materials (e.g., packaging cell lines, helper viruses, and vector constructs). See, for example, Gene *Therapy Protocols* (*Methods in Molecular Medicine*), edited by Jeffrey R. Morgan, Humana Press, Totowa, NJ (2002) and *Viral Vectors for Gene Therapy: Methods and Protocols*, edited by Curtis A. Machida, Humana Press, Totowa, N.J. (2003). Virus-based nucleic acid delivery vectors are typically derived from animal viruses, such as adenoviruses, adeno-associated viruses, retroviruses, lentiviruses, vaccinia viruses, herpes viruses, and papilloma viruses. Lentiviruses are a genus of retroviruses that can be used to infect cells. Adenoviruses contain a linear double-stranded DNA genome that can be engineered to inactivate the ability of the virus to replicate in the normal lytic life cycle. Adenoviruses and adeno-associated viruses can be used to infect cells.

Vectors for nucleic acid delivery can be genetically modified such that the pathogenicity of the virus is altered or removed. The genome of a virus can be modified to increase infectivity and/or to accommodate packaging of a nucleic acid, such as a nucleic acid encoding a NAP-2 polypeptide, a TGF-α polypeptide, and/or an ErBb3 polypeptide (or a fragment thereof). A viral vector can be replication-competent or replication-defective, and can contain fewer viral genes than a corresponding wild-type virus or no viral genes at all.

In addition to nucleic acid encoding a NAP-2 polypeptide, a TGF-α polypeptide, and/or an ErBb3 polypeptide (or a fragment thereof), a viral vector can contain regulatory elements operably linked to a nucleic acid encoding the polypeptide(s) (or a fragment thereof). Such regulatory elements can include promoter sequences, enhancer sequences, response elements, signal peptides, internal ribosome entry sequences, polyadenylation signals, terminators, or inducible elements that modulate expression (e.g., transcription or translation) of a nucleic acid. The choice of element(s) that may be included in a viral vector depends on several factors, including, without limitation, inducibility, targeting, and the level of expression desired. For example, a promoter can be included in a viral vector to facilitate transcription of a nucleic acid encoding a NAP-2 polypeptide, a TGF-α polypeptide, and/or an ErBb3 polypeptide. A promoter can be constitutive or inducible (e.g., in the presence of tetracycline), and can affect the expression of a nucleic acid encoding a NAP-2 polypeptide, a TGF-α polypeptide, and/or an ErBb3 polypeptide in a general or tissue-specific manner. Tissue-specific promoters include, without limitation, a cardiac-specific MHC promoter, a troponin promoter, and an MLC2v promoter.

As used herein, "operably linked" refers to positioning of a regulatory element in a vector relative to a nucleic acid in such a way as to permit or facilitate expression of the encoded polypeptide. For example, a viral vector can contain a cardiac-specific promoter and a nucleic acid encoding a NAP-2 polypeptide, a TGF-α polypeptide, and/or an ErBb3 polypeptide. In this case, a cardiac-specific MHC promoter is operably linked to a nucleic acid encoding a NAP-2 polypeptide, a TGF-α polypeptide, and/or an ErBb3 polypeptide such that it drives transcription in cardiac cells.

In some cases, a nucleic acid encoding a NAP-2 polypeptide, a TGF-α polypeptide, and/or an ErBb3 polypeptide (or a fragment thereof) can be administered to cells using non-viral vectors. Methods of using non-viral vectors for nucleic acid delivery are known to those of ordinary skill in the art. See, for example, *Gene Therapy Protocols* (*Methods in Molecular Medicine*), edited by Jeffrey R. Morgan, Humana Press, Totowa, N.J. (2002). For example, a nucleic acid encoding a NAP-2 polypeptide, a TGF-α polypeptide, and/or an ErBb3 polypeptide can be administered to a mammal by direct injection of nucleic acid molecules (e.g., plasmids) comprising nucleic acid encoding a NAP-2 polypeptide, a TGF-α polypeptide, and/or an ErBb3 polypeptide, or by administering nucleic acid molecules complexed with lipids, polymers, or nanospheres.

A nucleic acid encoding a NAP-2 polypeptide, a TGF-α polypeptide, and/or an ErBb3 polypeptide (or a fragment thereof) can be produced by standard techniques, including, without limitation, common molecular cloning, polymerase chain reaction (PCR), chemical nucleic acid synthesis techniques, and combinations of such techniques. For example PCR or RT-PCR can be used with oligonucleotide primers designed to amplify nucleic acid (e.g., genomic DNA or RNA) encoding a NAP-2 polypeptide, a TGF-α polypeptide, and/or an ErBb3 polypeptide (or a fragment thereof).

In some cases, a patient at risk of experiencing a major adverse cardiac event (e.g., a patient identified as being likely to experience a major adverse cardiac event as described herein) can be treated by reducing the level of expression of one or more (e.g., one, two, three, four, five, six, seven, eight, nine, ten, or more) of the following polypeptides: eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, and/or MMP-3 polypeptides. A reduction in the level of one or more of these polypeptides can be used to reduce scar size and tissue remodeling and to improve cardiac function. For example, an area of fibrosis reflecting scar size from injury can be reduced by 10 to 100 percent (e.g., by 10 to 90 percent, by 10 to 80 percent, by 10 to 70 percent, by 10 to 60 percent, by 10 to 50 percent, by 20 to 100 percent, by 30 to 100 percent, or by 20 to 60 percent) following administration of a composition designed to reduce eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, and/or MMP-3 polypeptide expression or activity. In some cases, cardiac tissue remodeling can be reduced by 10 to 100 percent (e.g., by 10 to 90 percent, by 10 to 80 percent, by 10 to 70 percent, by 10 to 60 percent, by 10 to 50 percent, by 20 to 100 percent, by 30 to 100 percent, or by 20 to 60 percent) following administration of a composition designed to reduce eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, and/or MMP-3 polypeptide expression or activity. Examples of improved cardiac function include, without limitation, increased survivorship, reduced hospitalization, symptom-free tolerance of physical activity, improved global physical fitness, improved cardiac ejection fraction, improved cardiac output, improved stroke volume, improved cardiac mass index, and reduced scar size.

In some cases, the level of eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, and/or MMP-3 polypeptide expression can be reduced by administering a composition containing an antisense or RNAi molecule (e.g., an siRNA molecule or an shRNA molecule) designed to reduce polypeptide expression of an eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, or MMP-3 polypeptide. In some cases, the level of eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, or MMP-3 polypeptide activity can be reduced by administering an inhibitor of eotaxin-3, cathepsin-S, DKK-1, follistatin, ST-2, GRO-α, IL-21, NOV, transferrin, TIMP-2, TNFαRI, TNFαRII, angiostatin, CCL25, ANGPTL4, or MMP-3 polypeptide activity.

The invention will be further described in the following examples, which do not limit the scope of the invention described in the claims.

EXAMPLES

Example 1

Differential Coronary Serum Proteome Signature in Humans Suffering from Acute Myocardial Infarction Identifies Vulnerable Patients Study Design Patients between 40 and 82 years of age underwent coronary thrombus aspirate prior to PCI for STEMI. Fresh coronary aspirates were stored in EDTA tubes and centrifuged at 4° C. Serum supernatant was collected, treated with protease inhibitor, split into working aliquots, flash frozen in liquid nitrogen, and stored at −80° C. within 60 minutes of coronary sampling. The Mayo Clinic Risk Model of MACE and TIMI scoring were utilized for stratification at the time of myocardial infarction, and patients identified as non-high risk were enrolled and followed (n=25). Those suffering from death, recurrent infarction, or heart failure (MACE) within a two-year follow-up were categorized as vulnerable (n=11), while those who did not were categorized as protected (n=14).

Proteomics Evaluation

Stored coronary serum samples were thawed only once and prepared for ELISA-based antibody array analysis (Quantibody Human Array-6000, RayBiotech) to quantify 280 distinct cytokines Serum samples were diluted 1:5 with sample diluent. Glass protein array slides were allowed to equilibrate and dry at room temperature for 45 minutes. Each chamber within the slide was blocked for 30 minutes. Standards for each cytokine were prepared as eight serial dilutions and added to respective chambers, while the remaining chambers received 100 μL of serum. Following overnight incubation at 4° C., slides were washed for a total of 35 minutes. A biotinylated labeling agent was added to each chamber and incubated overnight at 4° C. Slides were washed for an additional 35 minutes and incubated with Cy3-Streptavidin for 1 hour protected from light at room temperature. Slides were washed and centrifuged for 3 minutes at 1,000 rpm. Dry slides were analyzed using Molecular Devices Axon GenePix Pro 6 software to generate a standard curve for each cytokine and determine individual concentrations in coronary serum.

Network Analysis

Differentially expressed array proteins were submitted for network analysis using Ingenuity Pathways Knowledge Base (IPKB, Ingenuity Systems, "www" dot "ingenuity.com") to identify associated functional sub-networks. These were merged into a composite interactome in IPKB and depicted using the network visualization program Cytoscape 2.8.2, with network topology characterized using Network Analyzer (Smoot et al., Bioinformatics, 27(3): 431-2 (2011)). Computed properties included node degree (k), degree distribution (P[k]), and clustering coefficient distribution (C[k]), the derivation of which were described elsewhere (Arrell et al., Stem Cells, 26(2):387-400 (2008)); Zlatkovic-Lindor et al., Stem Cells, 28(8):1355-67 (2010); and Crespo-Diaz et al., Cell Transplant., 20(6):797-811 (2011)). IPKB also prioritized over-represented molecular and physiological functions and canonical pathways associated with the resolved interaction network.

Animal Studies

Surgery was performed on 48 mice age 8-to 12-week old C57BL/6 under 1-2% isoflurane. Left anterior descending artery (LAD) was temporarily ligated for 60 minutes with the animal anesthetized throughout this time period. This was followed by restoration of blood flow for 5-10 minutes. Region supplied by LAD was then injected 5 times with 2.5 μL of saline or growth factors. The concentrations used for NAP-2 and TGF-α injections were 5-25 ng per injection and 4-20 ng per injection, respectively.

Pain prophylaxis was implemented by an acetaminophen regimen (100-300 mg/kg in drinking water) for 2 days prior to and 5 days after surgery. Prior to surgery, mice were randomized into saline (n=12) or growth factor treated (n=6) groups in 2:1 format. Individuals involved in performing the surgery and collecting and analyzing echocardiographic data were blinded throughout the study. Cardiac function and structure were quantified prospectively by echocardiography using a 30 MHz transducer up to 1 month following ischemia reperfusion injury. Ejection fraction was defined as [(LVVd−LVVs)/LVVd]×100, where LVVd is LV end-diastolic volume, and LVVs is LV end-systolic volume.

Statistical Analysis

This work was designed to assess the serological changes in the concentration of 280 cytokines Patient clinical data were analyzed as mean±SD and compared between groups with 2-sample student t-test or median±interquartile range. Cytokine concentrations were presented as median±interquartile range, and analyzed by non-parametric statistics Mann-Whitney U test. Differences were considered significant with $p<0.05$. Receiver operating characteristic (ROC) curves were constructed to evaluate the prognostic potential of each cytokine for STEMI patient stratification prior to PCI. Network analysis p-values were calculated using Fisher's exact test, determining the probability that association between dataset proteins and functions or canonical pathways is explained by chance alone. Statistical analyses were performed in SAS JMP 9.0 and MedCalc software, version 12.2.1.

Results

Coronary Serum Molecular Fingerprinting

Coronary thrombus aspirate was obtained from STEMI patients with an occlusive coronary lesion. Thrombectomy was performed prior to PCI with a drug-eluting stent (FIG. 1A). Patient aspirates were included in the study if coronary intervention was without complication and restored from TIMI-0 to TIMI-3 flow. All patients were managed according to ACC/AHA practice guidelines (Kushner et al., J. Am. Coll. Cardiol., 54(23):2205-41 (2009)). Aspirated thrombus and coronary blood was processed for plasma extraction and subjected to proteomic assessment with generation of a heat map plotting the plasma protein expression profile for each patient (FIG. 1B).

Discrimination of Vulnerable Versus Protected STEMI Cohorts

Figure 2:
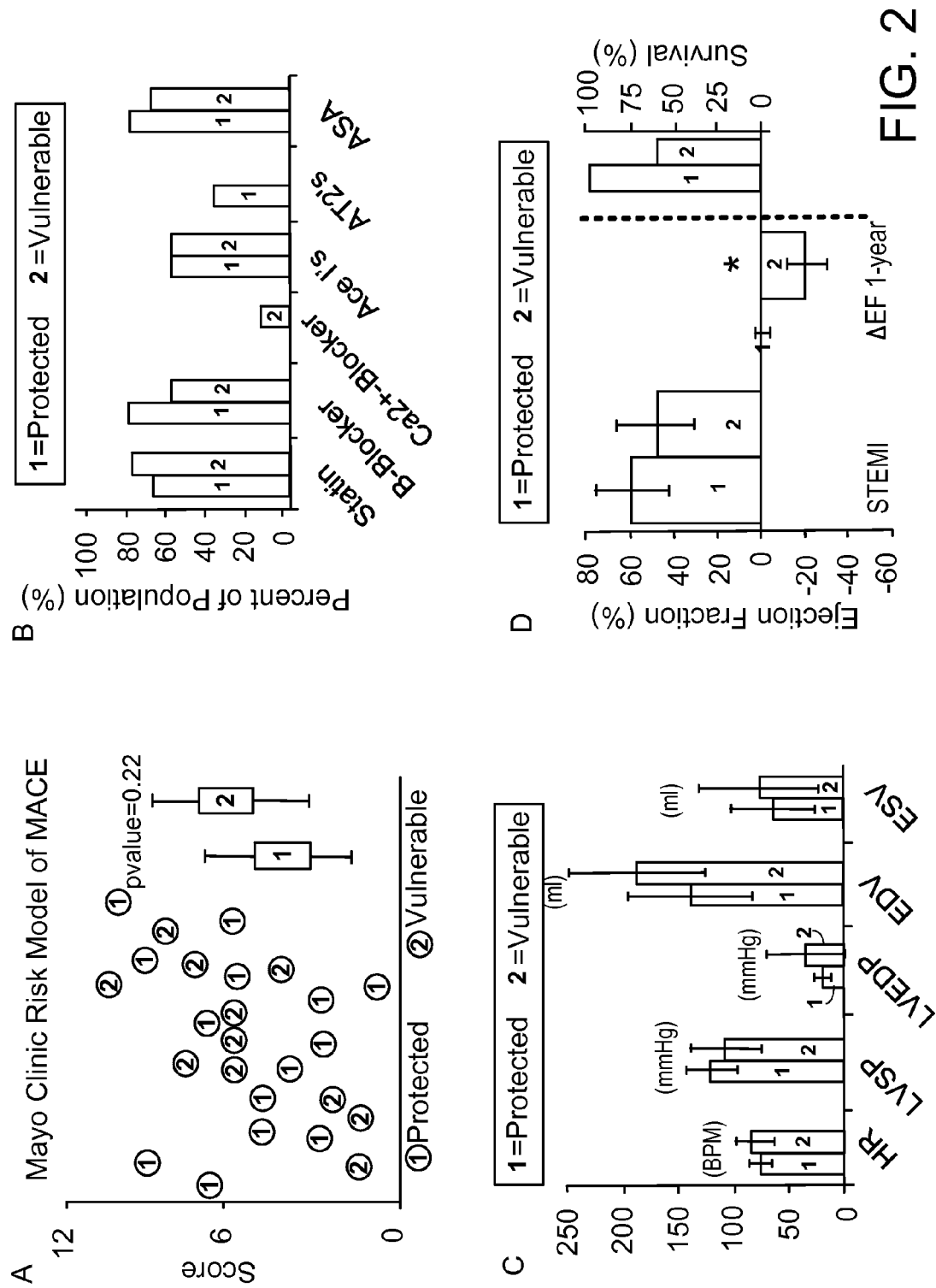
FIGS. 2A-2D provide a clinical assessment of protected and vulnerable patient cohorts.

During a 2-year follow-up period, patients with major cardiac adverse events were categorized as vulnerable (n=11), and those without were categorized as protected (n=14). No differences in demographics and cardiovascular health factors (Table 1) were noted between the two cohorts. Several risk stratification models were calculated for each patient. Specifically, TIMI risk score for probability of death during hospitalization and up to 6-months was low in both patient cohorts (5.5±2 in vulnerable and 4±4.5 in protected, p=0.08) (Table 1) (Morrow et al., JAMA, 286(11):1356-9 (2001) and Morrow et al., Circulation, 102(17):2031-7 (2000)). The Mayo Clinic Risk Model of MACE validated TIMI scoring, placing both groups in the non-high risk category (5.5±3 in vulnerable and 4±2 in protected, p=0.22) (FIG. 2A) (Singh et al., J. Am. Coll. Cardiol., 40(3):387-93 (2002)). Echocardiographic evaluation, however, revealed severe reduction in ejection fraction (−18±7%) in the vulnerable group compared to limited change (−0.5±2.2%) in the protected group (FIG. 2D; $p<0.05$). Survivorship was 65% in the vulnerable versus 100% in the protected group (FIG. 2D).

TABLE 1

Baseline characteristics of STEMI patient group.

| Baseline Characteristics | Protected cohort n = 14 | Vulnerable cohort n = 11 |
|---|---|---|
| Age in years | 67 (8) | 69.5 (10) |
| Women, % | 50% | 40% |
| Troponin levels, median ng/ml | 4 (3.22) | 8 (16.3) |
| C-reactive protein, mg/liter | 3 (11.4) | 3 (12.3) |
| TIMI Risk Index | 3 (3.5) | 5.5 (3.5) |
| WBC levels | 11620 (3790) | 12795 (8223) |
| MI presentation to Balloon, hrs | 6 hrs | 5 hrs |
| NYHA Score, median | 1 (0.5) | 1 (0.75) |
| Past family history CAD | 5 | 2 |
| Hypercholesterolemia | 4 | 4 |
| Hypertension | 5 | 2 |
| Smoking | 4 | 1 |
| Diabetes Mellitus | 1 | 2 |

Proteomics Dissection Uncovers Vulnerability Biomarkers

Coronary serum aspirates from each patient were evaluated for protein content. Standard curves for each of the 280 probes, constituting a comprehensive cytokine panel, were generated to determine concentration. Initially, a $p \leq 0.075$ cutoff was utilized to capture a spectrum of candidate cytokines with differential concentrations in protected versus vulnerable patient samples. These included eotaxin-3, cathepsin-S, Dickopf-1 (DKK-1), follistatin, suppression of tumorigenicity-2 (ST-2), GRO-alpha (GRO-α), interleukin-21 (IL-21), nephroblastoma overexpressed (NOV), transferrin, tissue inhibitor of metallopeptidase-2 (TIMP-2), tumor necrosis factor receptor-1 and -2 (TNFαRI and II), erythroblastic leukemia viral oncogene-3 (ErBb3), neutrophil-activating protein-2 (NAP-2), angiostatin, chemokine ligand-25 (CCL25), angiopoietin like-4 (ANGPTL4), matrix metalloproteinase-3 (MMP-3) and transforming growth factor-α (TGF-α) (FIGS. 3A and 4-10).

Figure 3:
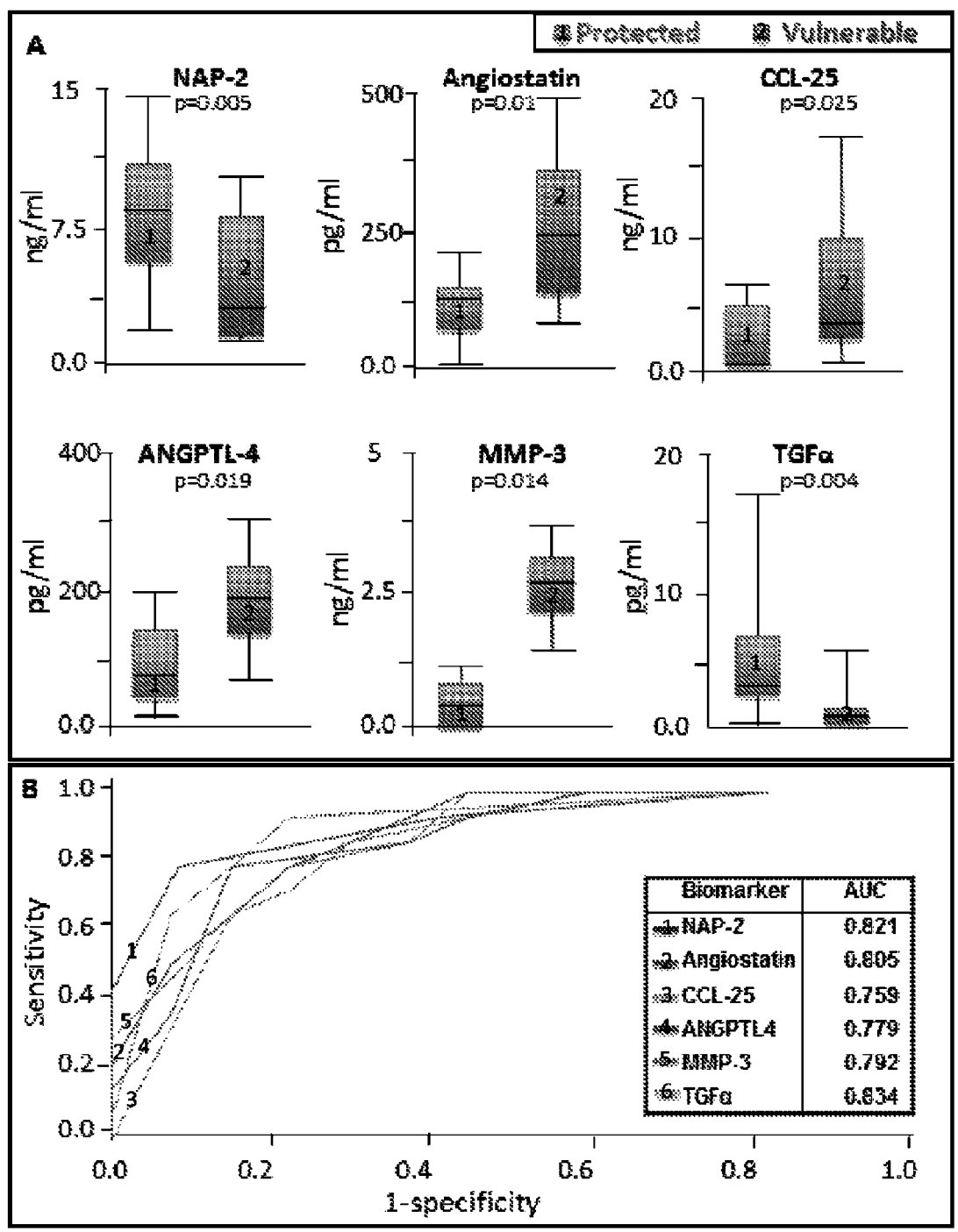
FIG. 3A provides the indicated cytokine concentrations in protected and vulnerable cohorts.
FIG. 3B provides ROC curves for each cytokine of FIG. 3A.
Figure 4:
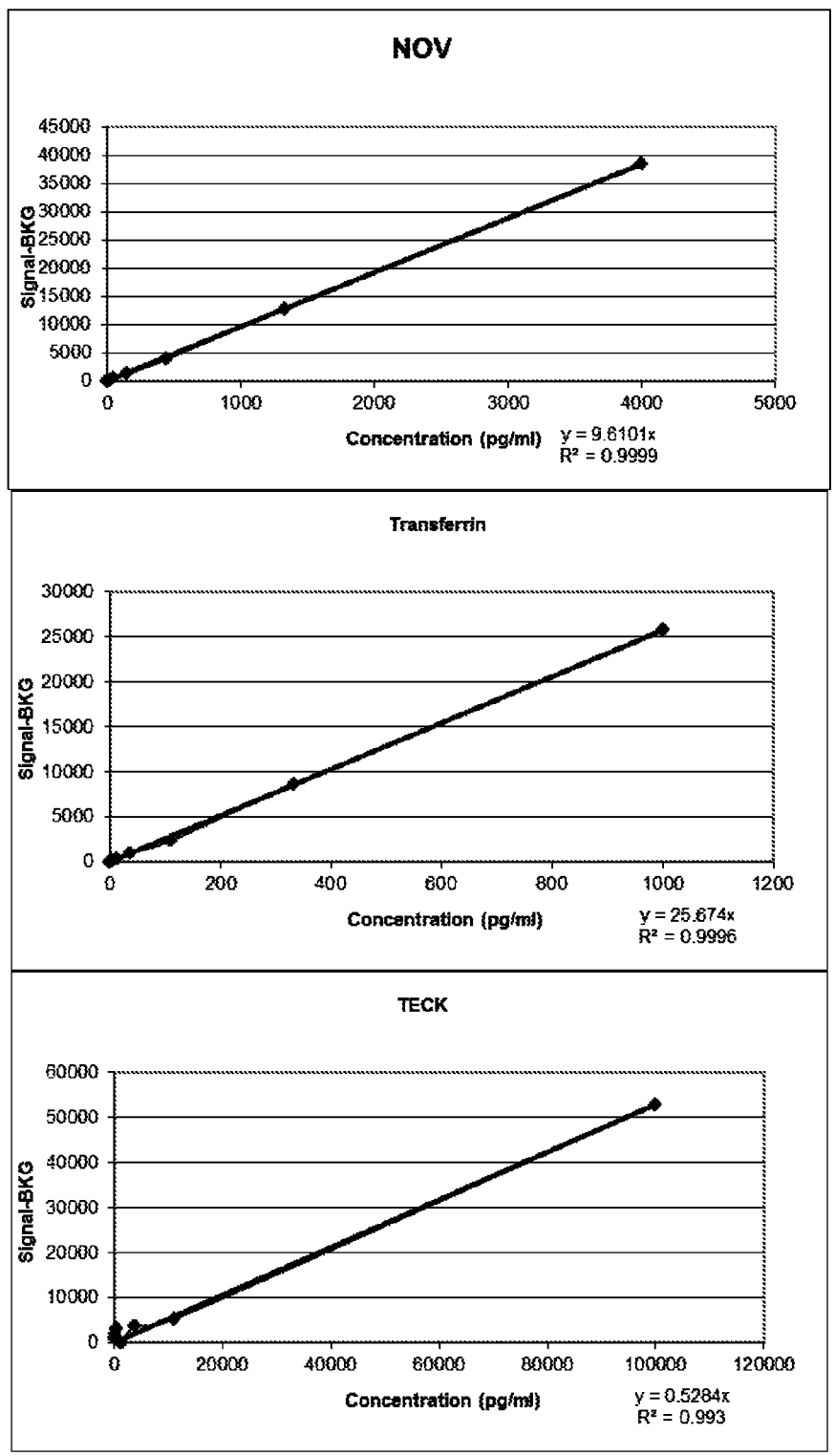
FIG. 4 contains bar graphs plotting standard curves for the indicated cytokine.
Figure 5:
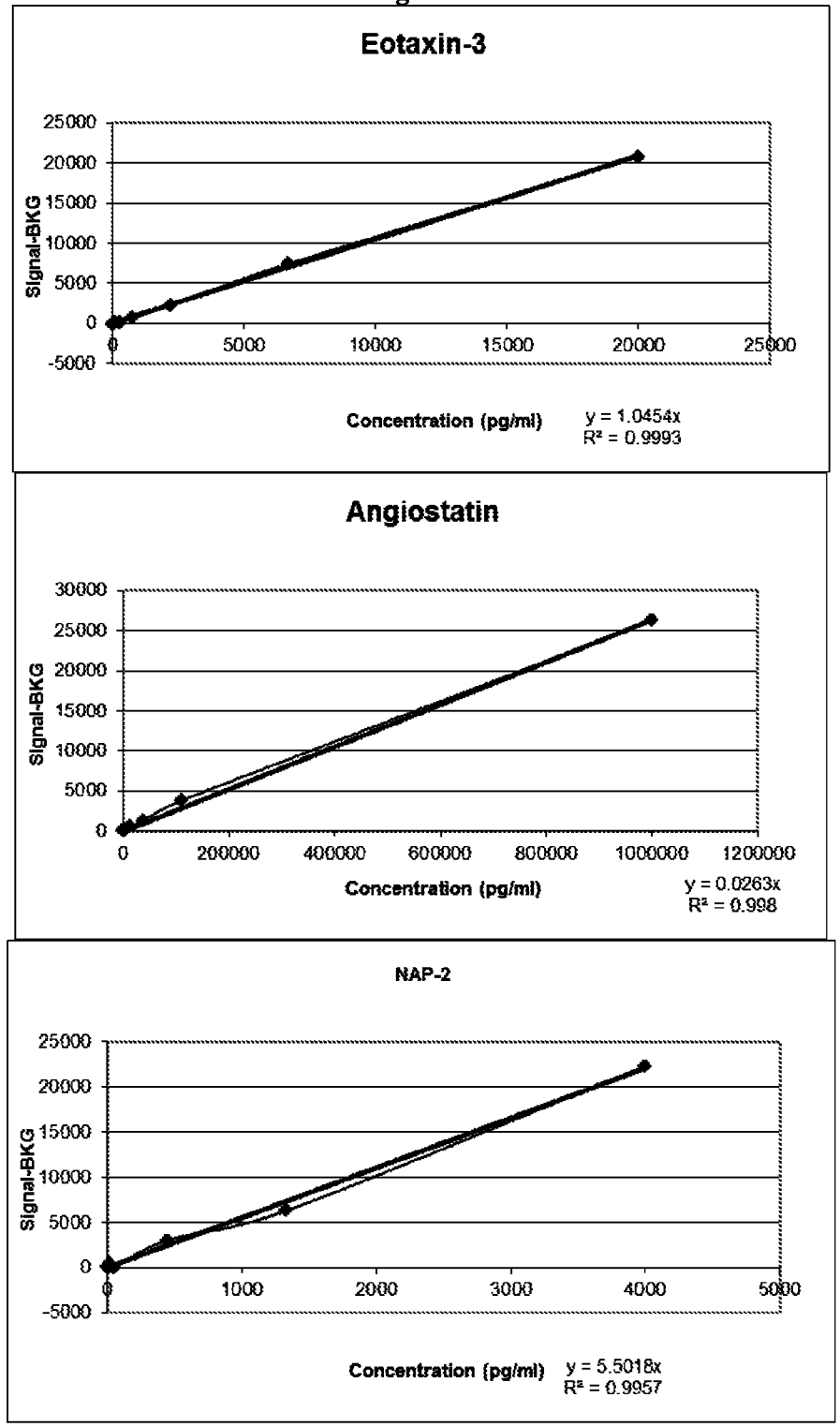
FIG. 5 contains bar graphs plotting standard curves for the indicated cytokine.
Figure 7:
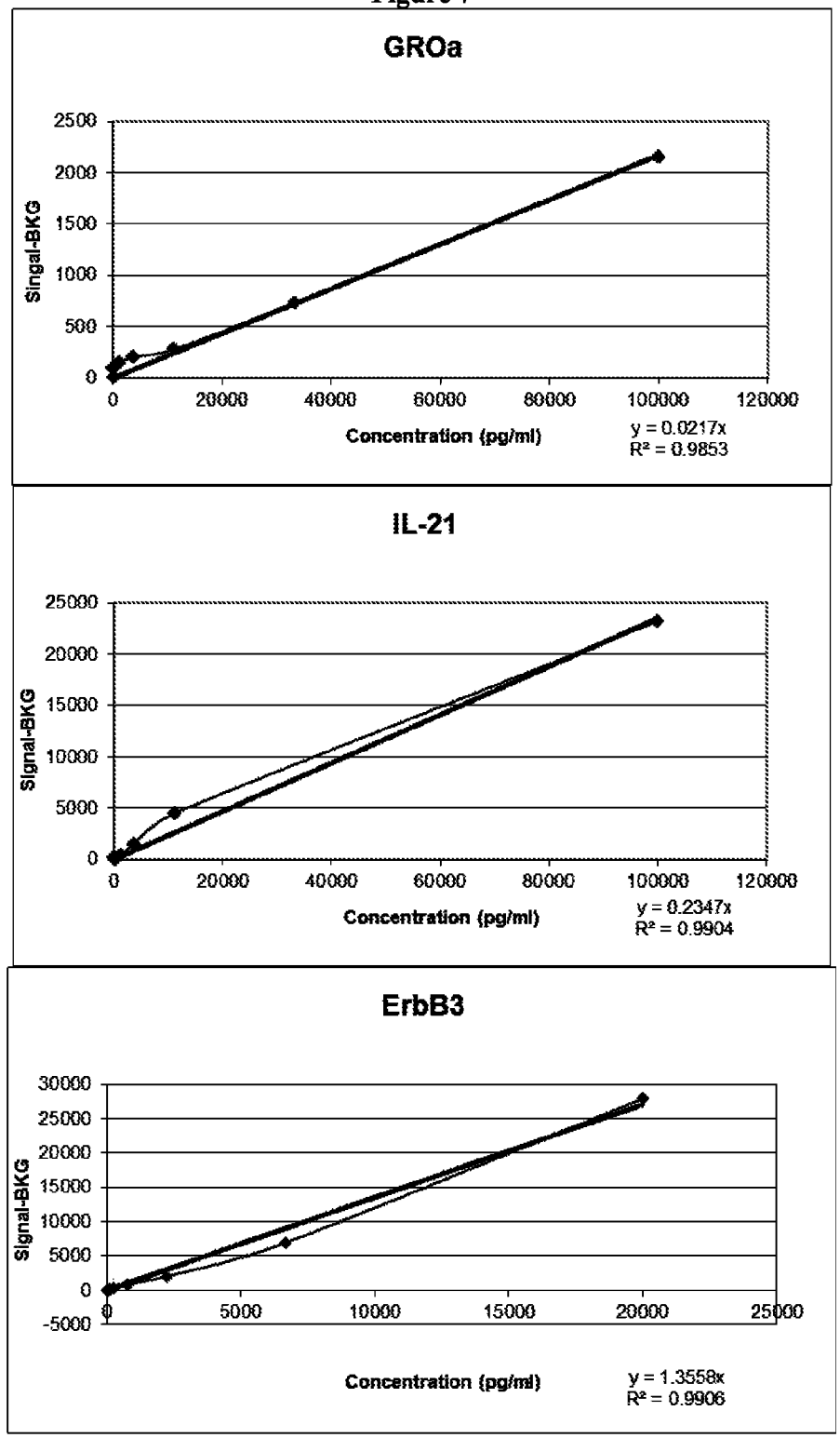
FIG. 7 contains bar graphs plotting standard curves for the indicated cytokine.
Figure 9:
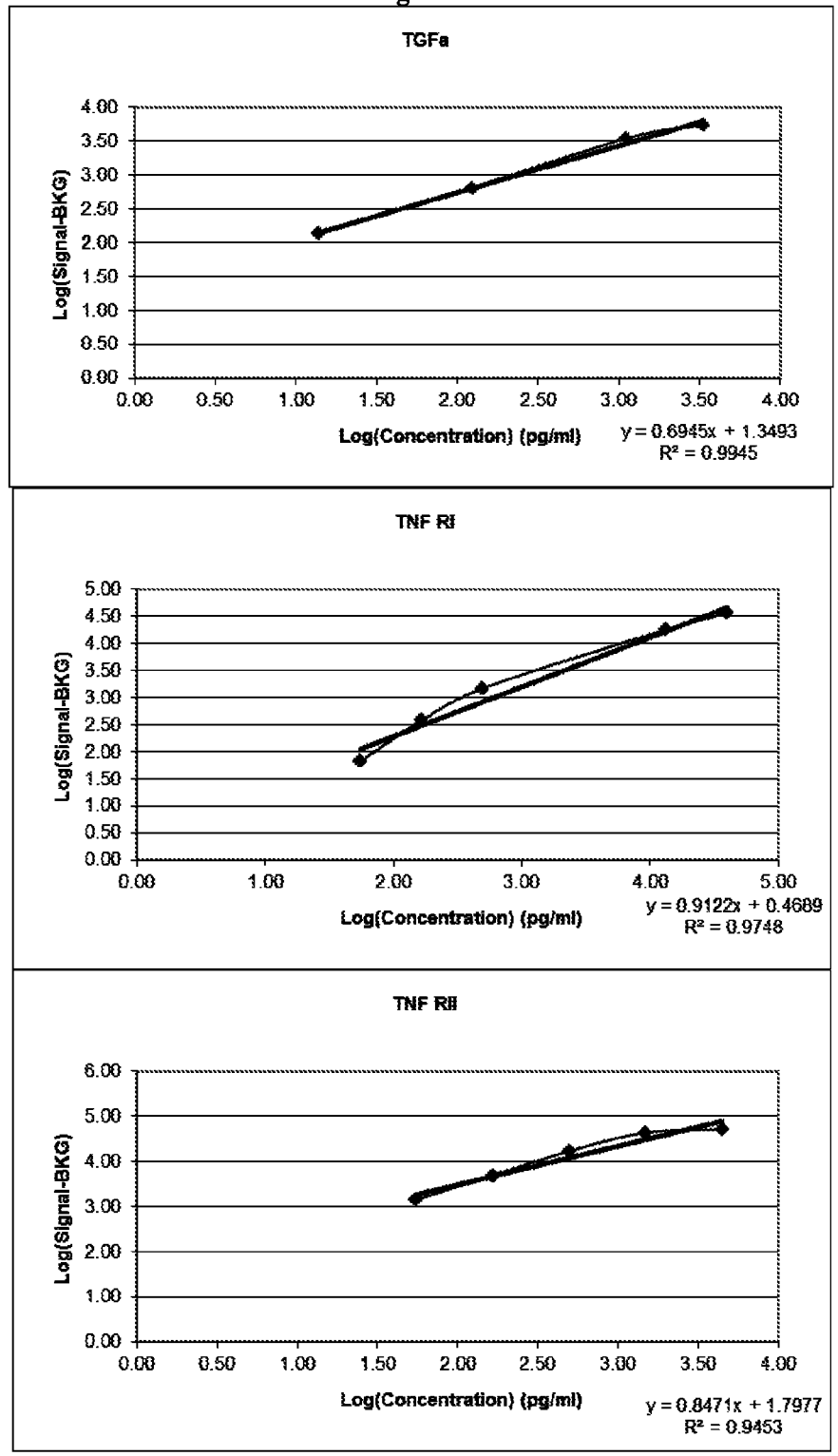
FIG. 9 contains bar graphs plotting standard curves for the indicated cytokine.
Figure 10:
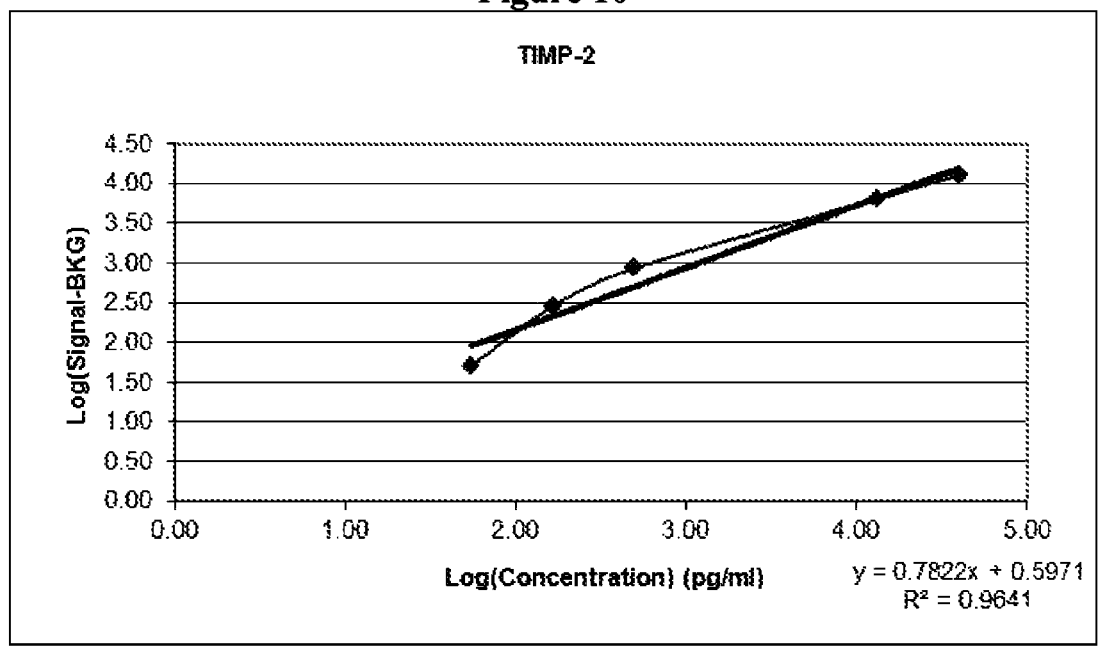
FIG. 10 contains bar graphs plotting standard curves for the indicated cytokine.
Figure 11:
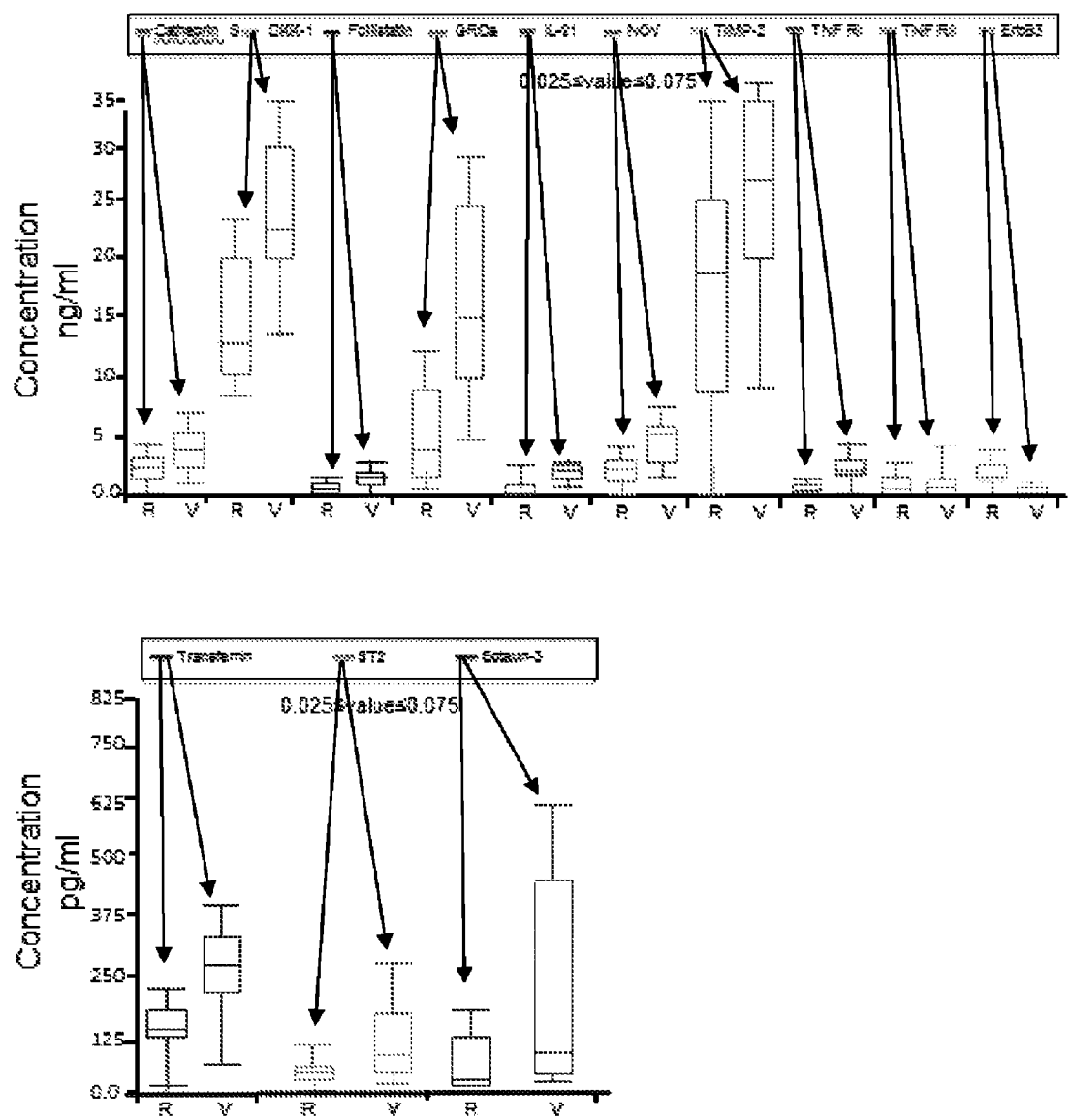
FIG. 11 contains bar graphs plotting cytokine concentrations in protected and vulnerable cohorts.
Figure 12:
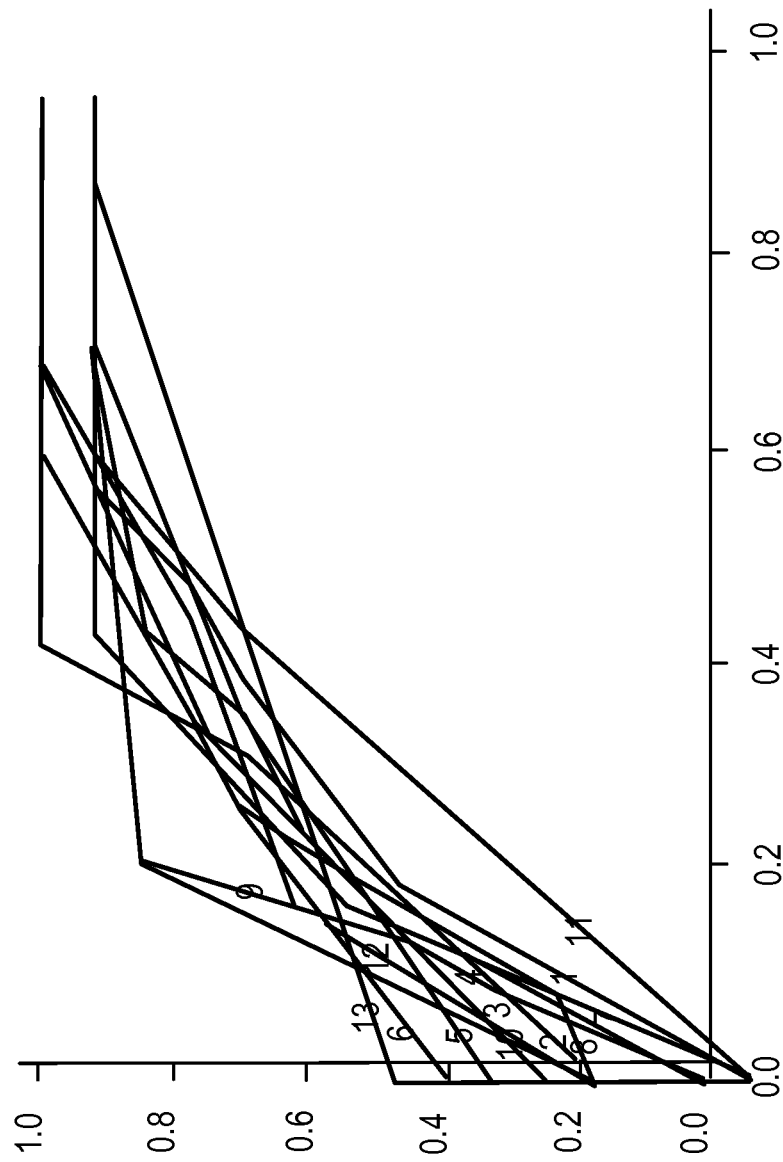
FIG. 12 contains ROC curves for the indicated cytokines.

The resulting 19 cytokines were subjected to a more discriminating cutoff (p≤0.025) yielding six cytokines, namely NAP-2, angiostatin, CCL25, ANGPTL4, MMP-3, and TGF-α. The median concentrations for each of the six resolved factors in the protected and vulnerable group were for: NAP-2 8.0 ng/mL and 5.0 ng/mL (p=0.005), Angiostatin 146 pg/mL and 242 pg/mL (p=0.01), CCL25 undetected and 3.8 ng/mL (p=0.025), ANGPTL4 73.3 pg/mL and 152 pg/mL (p=0.019), MMP-3 884 pg/mL and 2.7 ng/mL (p=0.014), and TGF-α 2.1 ng/mL and undetected (p=0.004), respectively (FIG. 3A). To probe the discriminatory potential of each factor, a receiver-operating-characteristic (ROC) curve was generated (FIG. 3B) yielding area under the curve (AUC) as follows: TGF-α 0.834 (p=0.0003), NAP-2 0.821 (p=0.0005), Angiostatin 0.805 (p=0.001), MMP-3 0.792 (p=0.003), ANGPTL4 0.779 (p=0.006) and CCL25 0.759 (p=0.009). This in turn allowed projection of sensitivity and specificity (Table 2). Concentration results (FIG. 11), ROC curves (FIG. 12), and sensitivity and specificity results (FIG. 13) for the remaining 13 factors (0.03≤p≤0.075) were obtained.

TABLE 2

Cytokines with projected sensitivity and specificity; and pathobiological role in myocardial infarction.

| Biomarker | Sensitivity (%) | Specificity (%) | Biological role in MI |
|---|---|---|---|
| NAP-2 | 80 | 90 | Activates leukocyte and endothelial cells within atherosclerotic plaque. |
| Angiostatin | 100 | 55 | Inhibits collateral coronary vasculature formation. |
| CCL-25 | 85 | 64 | Attracts macrophages and other inflammatory cells towards atherosclerotic plaque. |
| ANGPTL-4 | 80 | 82 | Potentially inhibits neovascularization. |
| MMP-3 | 80 | 73 | Extracellular matrix remodeling, associated with left ventricular dysfunction. |
| TGFα | 93 | 73 | Used to stimulate stem cell secretion of VEGF to improve myocardial function post-MI. |

Systems Biology Maps Over-represented Processes in MACE-Prone Individuals

Figure 14:
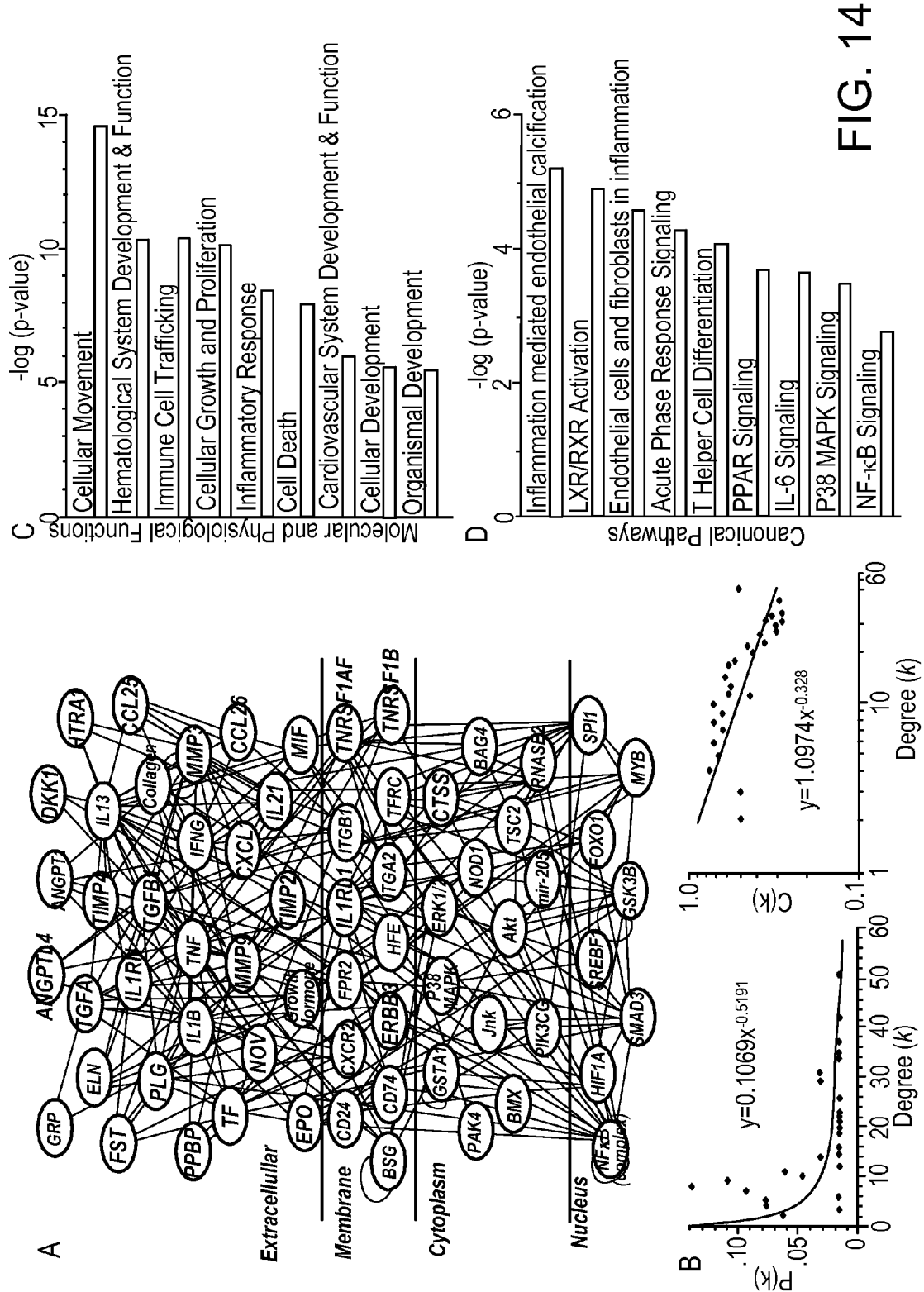
FIG. 14A is a diagram of an interaction network of 19 identified cytokines (bold font).
FIG. 14B is a network degree distribution, (P[k]) versus degree (k), and clustering coefficient distribution, (C[k]) versus (k), indicating non-stochastic scale-free network architecture and network hierarchical tendencies, respectively.
FIG. 14C is a bar graph of prioritized molecular and physiological functions.
FIG. 14D is a bar graph of prioritized canonical pathways.

The biological relationship between all discriminatory polypeptides was probed using complex network analysis. These 19 factors clustered into an organized network composed of 65 nodes linked by 417 pairwise connections (FIG. 14A). Network topology displayed non-stochastic architecture with hierarchical tendencies (FIG. 14B). Evaluation of over-represented molecular and physiological functions revealed prioritization for hematological, immunological, and cardiovascular functions (FIG. 14C). Canonical pathway assessment ranked calcium regulation, retinoic acid signaling, and endothelial inflammation as the most highly correlated to the resolved network (FIG. 14D). Thus, derivation of the non-stochastic network encompassing 19 factors identified within the coronary serum, maps activated pathophysiological processes discriminating vulnerable from protected patients at the time of STEMI.

Figure 15:
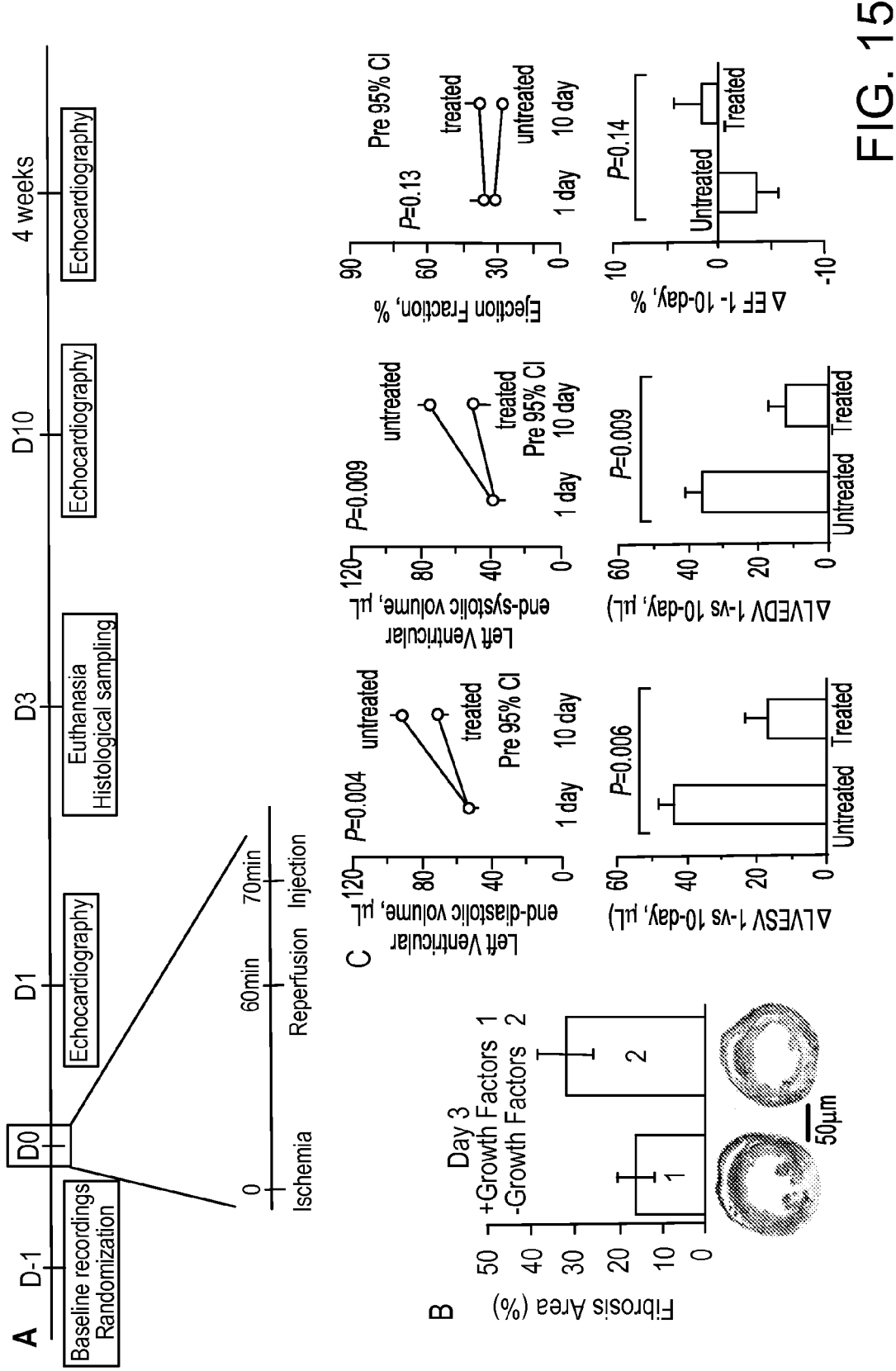
FIGS. 15A-15C demonstrate the functional analysis of coronary bed proteins in cardiac ischemia reperfusion injury.

Therapeutic effect of coronary serum protein in ischemia reperfusion injury The day before surgery 48 baseline echocardiographic recordings were collected, and the mice were randomized 2:1 into saline and growth factor treated groups. After ischemia reperfusion injury was induced, 5-25 ng of NAP-2 and 4-20 ng TGF-α were injected in the region supplied by LAD (FIG. 15A). Three days later, hearts we harvested, and fibrosis was quantified on saline (n=20) and growth factor (n=10) treated groups. Hearts treated with growth factors exhibited 14.3±6.2% of fibrosis in the left ventricular wall compared to 33.8±8.37% in the saline group (p=<0.01) (FIG. 15B).

Echocardiography collection was performed 1 and 10 days, and 4 weeks following injury (FIG. 15A). Significant improvement was observed during the acute phases of injury (FIG. 15C) in growth factor treated mice. Left ventricular end-diastolic and systolic volumes were significantly improved in the growth factor treated cohort, demonstrating reduced remodeling and organ decompensation. These results demonstrate that factors within the coronary bed can be used as molecular therapy to reduce scar size, limit tissue remodeling and improve cardiac function following STEMI.

Taken together, these results demonstrate that markers such as the 19 cytokines described herein can be used to assess long-term outcomes following infarction. High-throughput proteomics thus can provide a molecular snapshot of disease entities at the tissue level. These results also demonstrate that treatment with NAP-2, TGF-α, or both during ischemia reperfusion injury can be used to reduce scar size and tissue remodeling, and to improve cardiac function. In addition, real-time monitoring of patient response to injury and/or treatment can be performed to inform personalized management at the time of reperfusion or during various treatment or post-treatment phases.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for improving cardiac function after myocardial infarction, wherein said method comprises administering a composition comprising a nucleic acid encoding a transforming growth factor-α (TGF-α) polypeptide and a nucleic acid encoding a neutrophil-activating protein-2 (NAP-2) polypeptide to a mammal, thereby improving cardiac function of said mammal.

2. The method of claim 1, wherein said mammal is a human.

3. The method of claim 1, wherein said method comprises administering said composition during a percutaneous coronary intervention.

4. A method for improving cardiac function after ischemia reperfusion injury, wherein said method comprises administering a composition comprising a nucleic acid encoding a transforming growth factor-α (TGF-α) polypeptide and a nucleic acid encoding a neutrophil-activating protein-2 (NAP-2) polypeptide to a mammal, thereby improving cardiac function of said mammal.

5. The method of claim 4, wherein said mammal is a human.

6. A method for improving cardiac function, wherein said method comprises administering a composition comprising a nucleic acid encoding a transforming growth factor-α (TGF-α) polypeptide and a nucleic acid encoding a neutrophil-activating protein-2 (NAP-2) polypeptide to a mammal, thereby improving cardiac function of said mammal, wherein said mammal is a human patient who underwent percutaneous coronary intervention for ST-elevation myocardial infarction.

* * * * *